(12) United States Patent
Zheng et al.

(10) Patent No.: US 9,737,265 B2
(45) Date of Patent: Aug. 22, 2017

(54) ADAPTIVE NOTCH FILTER

(75) Inventors: Ling Zheng, Acton, MA (US); Yu Chen, Andover, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 865 days.

(21) Appl. No.: 14/112,154

(22) PCT Filed: Apr. 20, 2012

(86) PCT No.: PCT/US2012/034354
§ 371 (c)(1),
(2), (4) Date: Oct. 16, 2013

(87) PCT Pub. No.: WO2012/145571
PCT Pub. Date: Oct. 26, 2012

(65) Prior Publication Data
US 2014/0039824 A1    Feb. 6, 2014

Related U.S. Application Data

(60) Provisional application No. 61/478,130, filed on Apr. 22, 2011.

(51) Int. Cl.
*A61B 5/00*  (2006.01)
*A61B 5/04*  (2006.01)
(Continued)

(52) U.S. Cl.
CPC ........ *A61B 5/7203* (2013.01); *A61B 5/04017* (2013.01); *A61B 5/0428* (2013.01); *H04B 1/109* (2013.01); *A61B 5/0472* (2013.01)

(58) Field of Classification Search
USPC ...................................................... 702/106
See application file for complete search history.

(56) References Cited

U.S. PATENT DOCUMENTS 5,058,139 A    10/1991  Egler
2005/0113704 A1  5/2005  Lawson et al.

FOREIGN PATENT DOCUMENTS

CN       1349393 A     5/2002
CN     201631188 U    11/2010
(Continued)

OTHER PUBLICATIONS

Khalid Mohamed Alajel, Remote Electrocardiogram Monitoring Based on the Internet, KMITL Sci. J. vol. 5 No. 2 Jan.-Jun. 2005, pp. 493-501.*

(Continued)

*Primary Examiner* — Tung Lau
(74) *Attorney, Agent, or Firm* — Jones Day

(57) ABSTRACT

A patient monitoring device and method that determines and monitors at least one patient parameter is provided. A configuration processor generates configuration information in response to a first input signal and an adaptive notch filter receives a second input signal. The second input signal includes a signal of interest and an interference signal in a predetermined frequency range. The adaptive notch filter automatically estimates the interference signal within the second input signal based on a filter parameter and removes the estimated interference signal from the second input signal to generate a target signal. A step processor is electrically coupled between the configuration processor and the adaptive notch filter and sets a value of the filter parameter based on the configuration information, wherein the adaptive notch filter uses the filter parameter to reduce a ringing artifact on the target signal below a threshold level.

25 Claims, 21 Drawing Sheets

(51) Int. Cl.
*A61B 5/0428* (2006.01)
*H04B 1/10* (2006.01)
*A61B 5/0472* (2006.01)

(56) References Cited

FOREIGN PATENT DOCUMENTS

JP          7-213494 A    8/1995
JP       2004-275563 A   10/2004

OTHER PUBLICATIONS

George Takla, The Problem of Artifacts in Patient Monitor Data During Surgery: A Clinical and Methodological Review, vol. 103, No. 5, Nov. 2006, p. 1196-1204.*
Understanding ECG Filtering, Mar. 10, 2014, 16 pages.*
Medical Definition of Electrocardiogram, printed on Feb. 13, 2017, 2 pages.*
Luo S. et. al., "A reivew of Electrocardiogram Filtering", Journal of elctrocardiology, Elsevier Science, XX, vol. 43, No. 6. Nov. 1, 2010, pp. 486-496, XP027442724 ISSN 0022-0736.
D. Rowell, "Introduction to Lease-Square Filters", MIT Opencourseware, Jan. 1, 2008, pp. 1-18 Retrieved from the Internet: URL:http/ocw.mit.edu/courses/mechanical-engineering/2-161-signal-processing-continuous-and-discrete-fall-2008/study-matierials/adaptivels.pdf.
Soo-Chang Pie et al., "Adaptive IIR Notch Filter Based on Least Mean P-Power Error Criterion" IEEE Transactions on Circuits and Systems II: Analog and DigitalSignal Processing, Institute of Electrical and Electronics Engineers, Inc. 345 Est 47th Street, New York, NY 10017, USA, vol. 40, No. 8, Aug. 1, 1993, pp. 525-529 XP000417927, ISSN:1057-7130, DOI: 10, 1109/82.242343 Abstract *11.2.3 Adatpive Method, pp. 592-593*.
Pomsathit A. et. al: "Variable Step-Size Algorithm for Lattice Form Structure Adaptive IIR Notch Filter", 2006 International Conference on Communications Circuits and Systems: Guilin, Guangxi, China, Jun. 25-28, 2006, IEEE Service Center, Piscataway, NJ Jun. 1, 2006, pp. 332-335, XP031010442, ISBN: 978--0-7803-9584-8, Abstract * II. The Previous Algorithm and proposed algorithm pp. 332-334*.

* cited by examiner

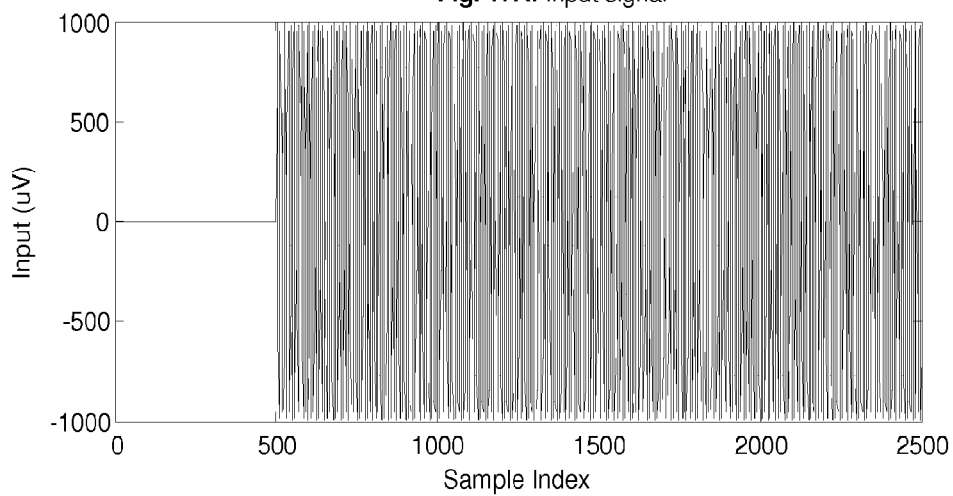
Fig. 17A: Input signal
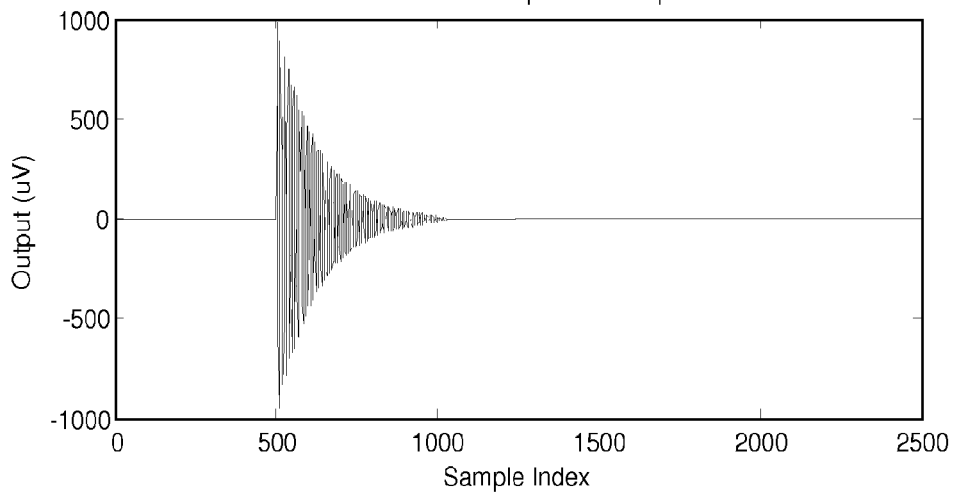
FIG 17B: Filter Output: Max step = 17.5uV
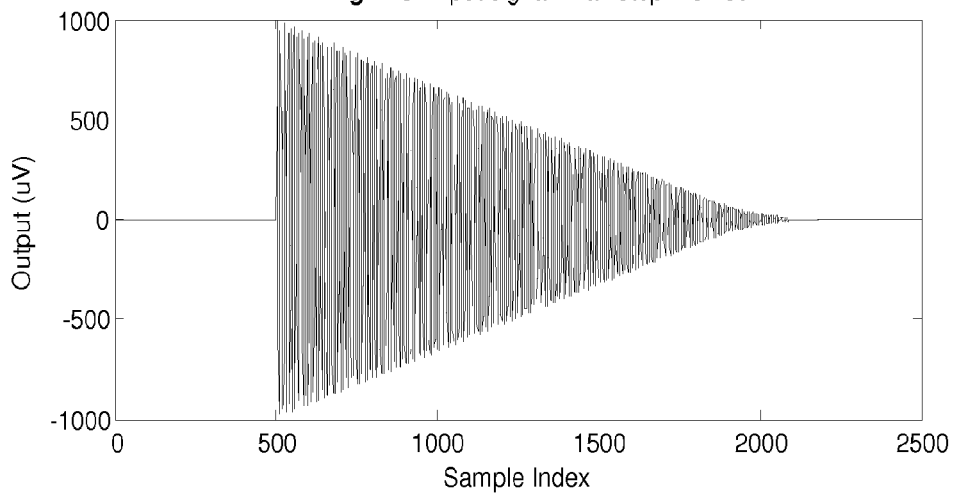
Fig 17C: Input signal: Max step = 0.78uV

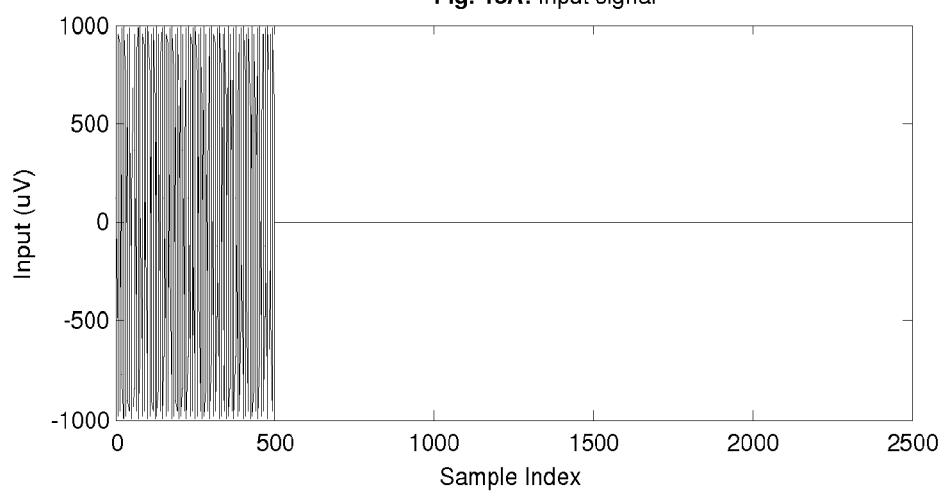
Fig. 18A: Input signal
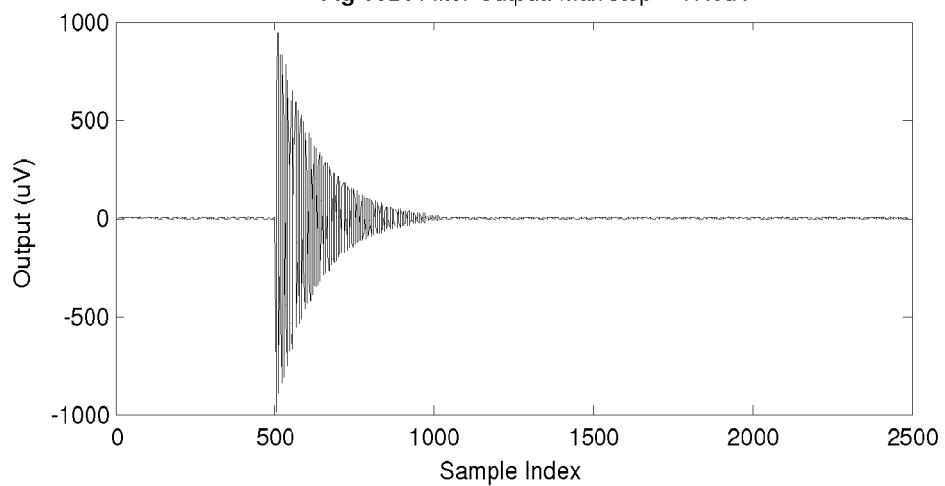
Fig 18B: Filter Output: Max step = 17.5uV
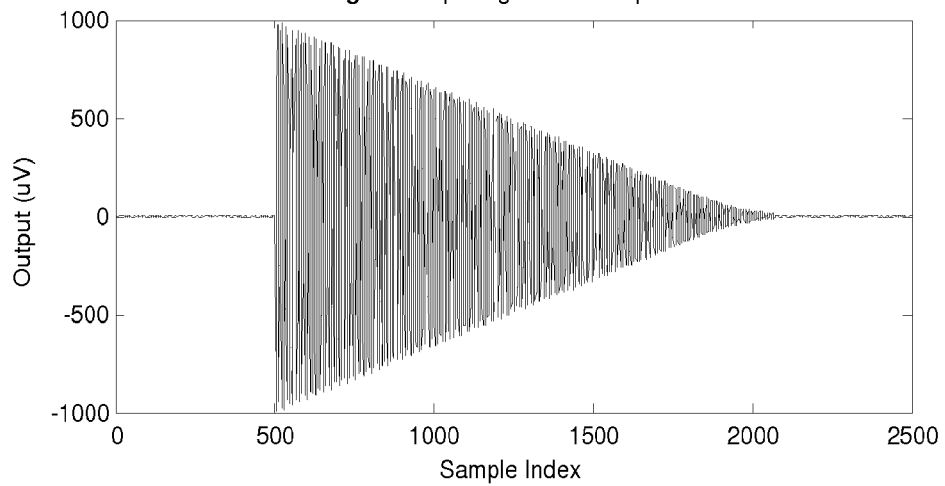
Fig 18C: Input signal: Max step = 0.78uV

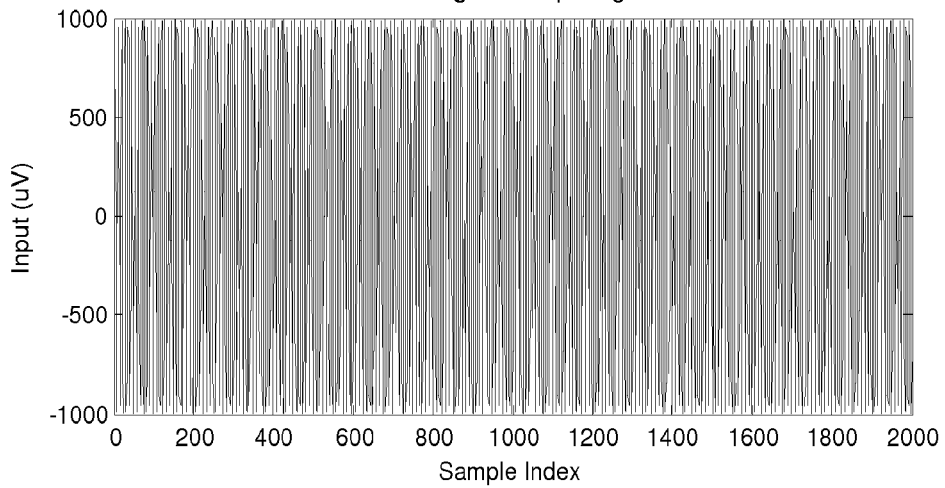
Fig. 19A: Input signal
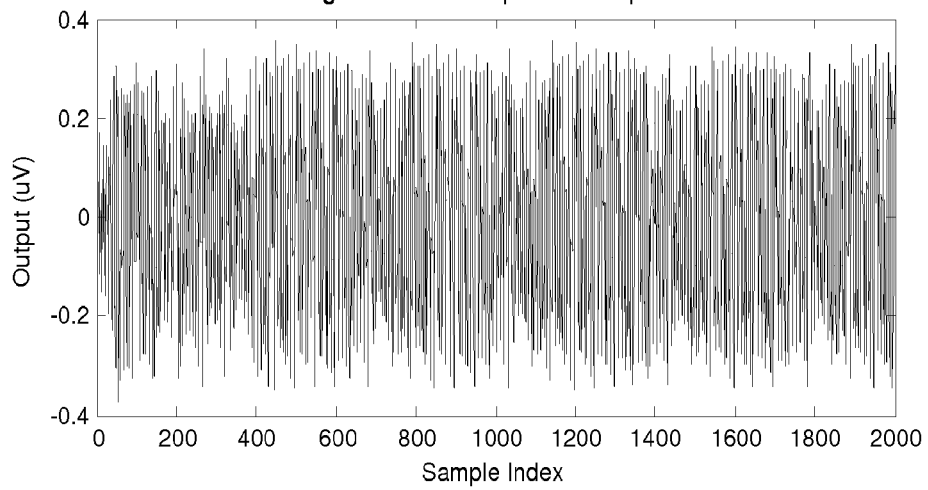
Fig. 19B: Filter Output: Max step = 17.5uV
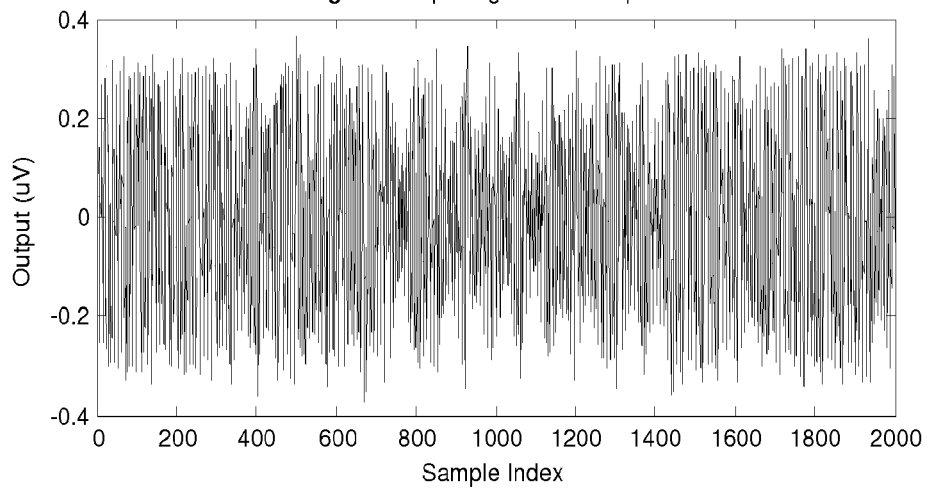
Fig. 19C: Input signal: Max step = 0.78uV

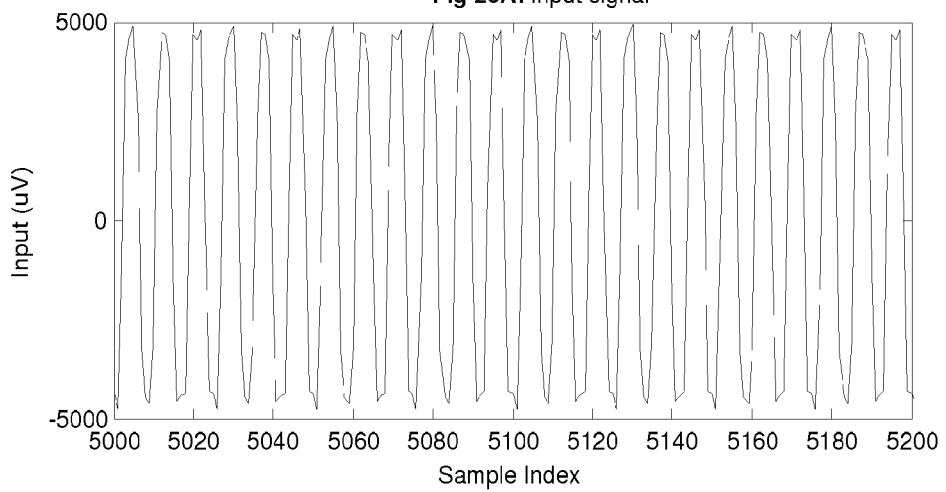
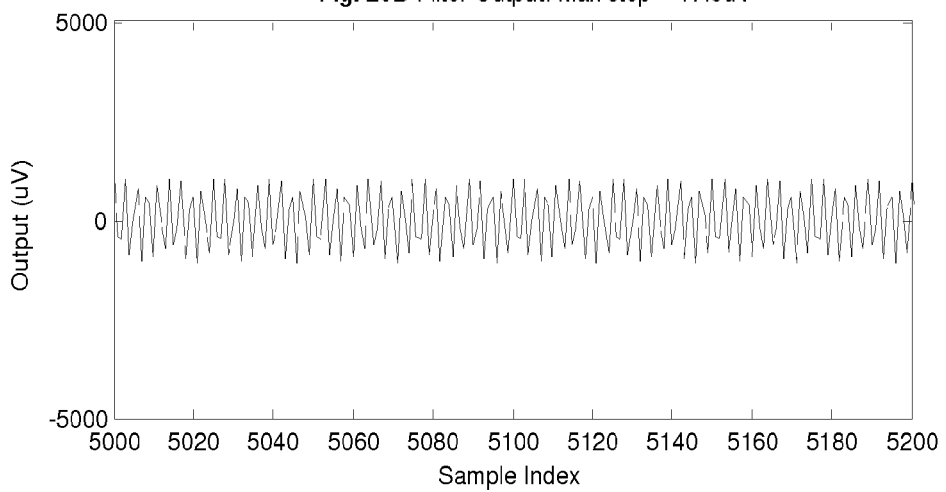
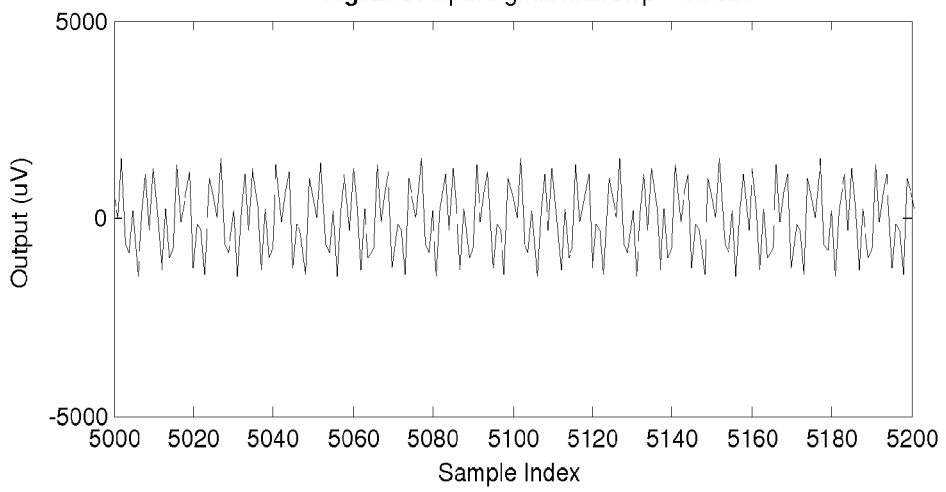

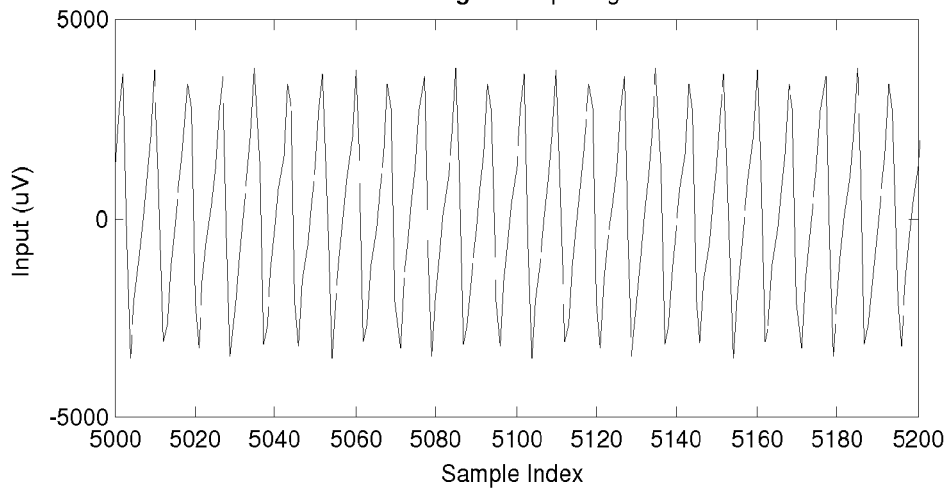
Fig. 21A Input signal
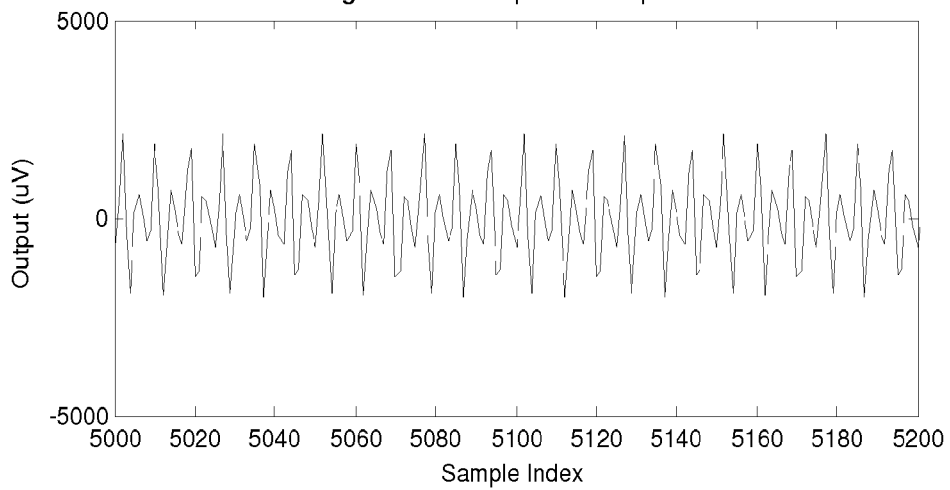
Fig. 21B Filter Output: Max step = 17.5uV
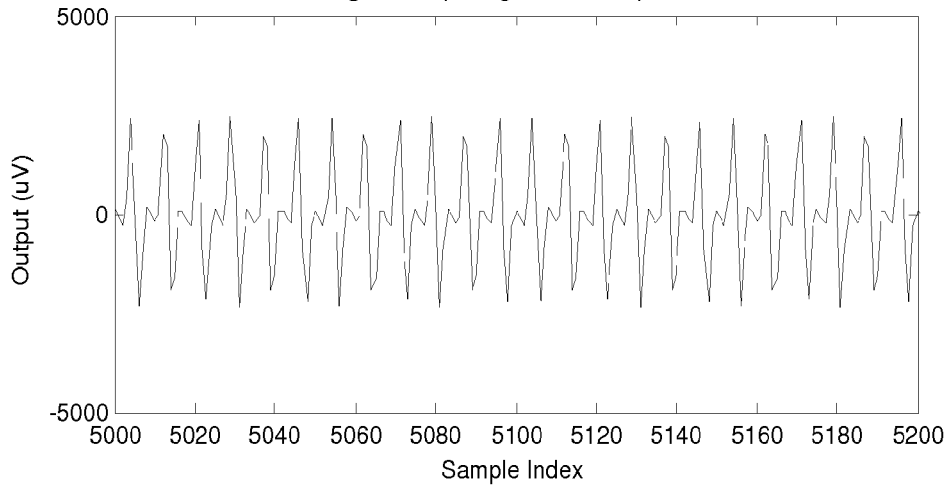
Fig. 21C Input signal: Max step = 0.78uV

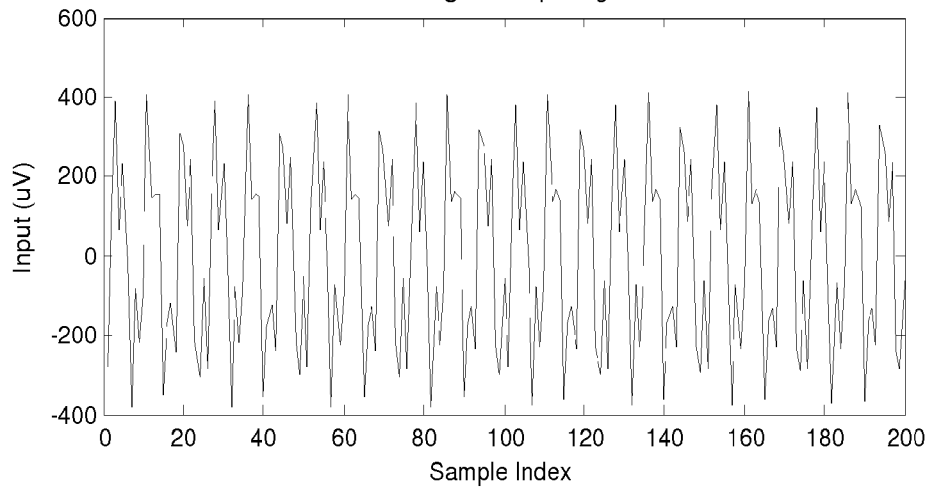
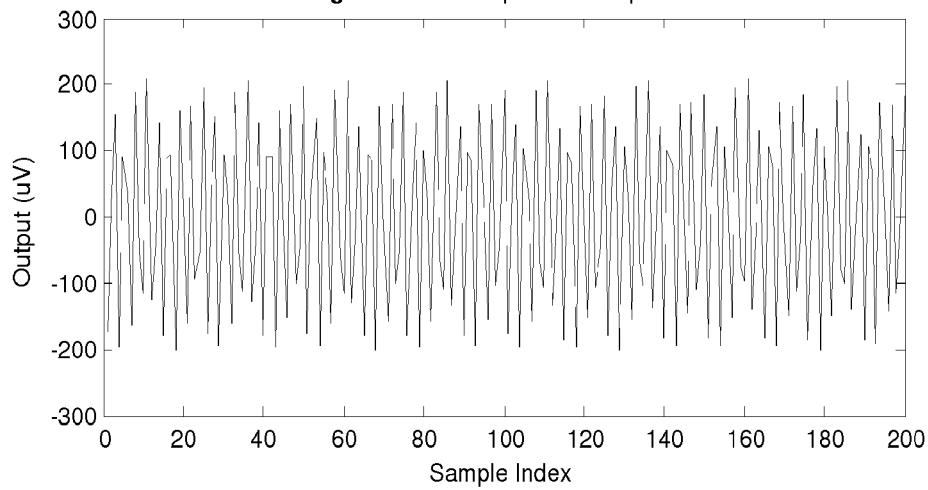
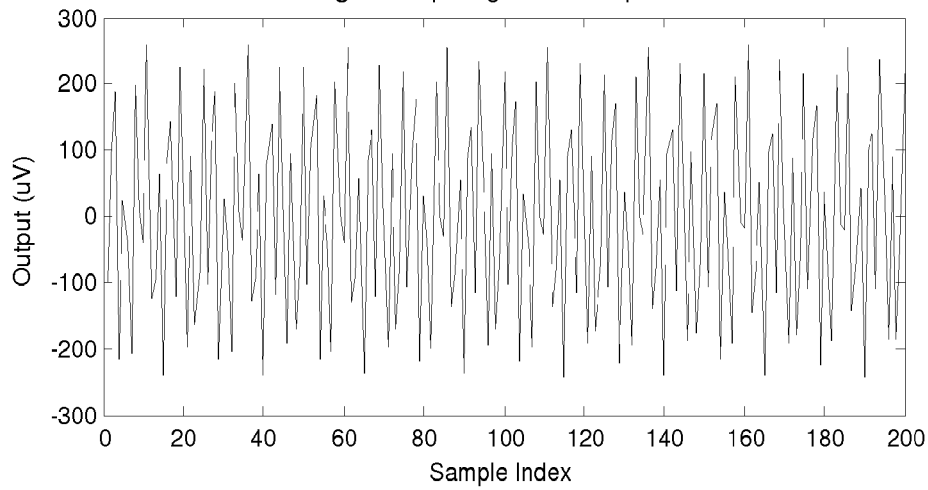

ADAPTIVE NOTCH FILTER

RELATED APPLICATIONS

This application is a National Stage application of PCT/US12/34354, filed Apr. 20, 2012, which claims priority from U.S. Provisional application 61/478,130, filed Apr. 22, 2011. The disclosures of the aforementioned applications are hereby incorporated by reference in their entireties.

FIELD OF THE INVENTION

This invention relates generally to an apparatus and method for reducing interference signals from sensed patient physiological signals in a patient monitoring device, and, more specifically, to an adaptive notch filter for use in a patient monitoring device that minimizes electrocardiogram (ECG) ringing.

BACKGROUND OF THE INVENTION

When providing healthcare to patients it is frequently important to accurately monitor at least one type of parameter associated with the patient. To accomplish this, at least one sensor is connected to a patient for use in sensing physiological signals that are provided to and interpreted by at least one type of patient monitoring device. The sensed physiological signals are used in determining the at least one patient parameter. Sensed signals having poor quality (e.g. interference from external sources) negatively impact the ability of the patient monitoring device to determine the desired patient parameter resulting in inaccurate patient parameter data values. Another problem associated with data obtained from a signal having poor quality relates to the use of inaccurate data for diagnostic purposes. Inaccurate patient parameter data derived from a signal having poor quality increases the likelihood of a false positive indication of a particular medical condition. To remedy these drawbacks, an adaptive notch filter has been developed and implemented in patient monitoring devices. A notch filter can effectively remove power line interference through a learning process whereby a step size of the notch filter is set enabling the notch filter to filter out the undesired portion of the input signal (e.g. external powerline interference). The step size is crucial to the performance of an adaptive algorithm. For example, a small step size rarely causes divergence, but takes long time to converge and a large step size converges quickly, but may cause divergence. Alternatively, using the larger step may also result in what is known as a "ringing artifact". It is therefore desirable to minimize ringing artifact while maximizing convergence of a filtered input signal.

FIG. 1 is a prior art block diagram of a conventional notch filter 100 that may be used to remove powerline noise from an input signal. The notch filter 100 may include a processor 102 that executes an adaptive algorithm that selectively estimates an amount of interference on an input signal x(n). The algorithm controls a summing function 104 to automatically filter the input signal x(n) by a certain value thereby removing the estimated interference therefrom. In operation, the primary input signal x(n) is the combination of the interested signal and interference. The processor 102 executes an adaptive algorithm to determine data representing an amount of estimated interference w(n) that is present in input signal x(n). An exemplary adaptive algorithm executed by the processor 102 may be found below in Table 1.

TABLE 1

| Notch Filter Pseudo-code | |
|---|---|
| W1 | w(n − 1) from previous iteration |
| w2 | w(n − 2) from previous iteration |
| y1 | y(n − 1) from previous iteration |
| fc = cos(2*pi*f0/fs) | f0 is the notch frequency |
| | fs is the sampling rate |
| for n = 1:N | Loop through all data samples |
|   y0 = x(n) − w1 | Input minus oscillation signal |
|   y(n) = y0 | Save filtered results to the output buffer |
|   d = y0 − y1 | Calculate error |
|   z = f(d) | Find step size. It is a function of d. |
|   w = 2*fc*w1 − w2 + z | Predict oscillator signal |
|   w2 = w1 | Shift oscillator samples |
|   w1 = w | Shift oscillator samples |
|   y1 = y0 | Shift output samples |
| end | End of the for-loop |

Upon determining the estimated interference w(n), the processor 102 provides the value w(n) to a negative input of the summing function 104. The summing function 104 automatically filters the subsequent input signal x(n) to remove the estimated interference from the input signal x(n) in order to generate an output signal y(n) which optimally only includes the interested signal. Thus, output signal y(n) represents the difference between input signal x(n) that includes both the interested signal and the interference and the estimated interference w(n) as determined by the processor 102. The processor 102 is able to selectively and continually adjust the value of estimated interference w(n) to reflect the optimal estimation of the interference to be removed from the input signal x(n).

In previous iterations, the notch filter may be a phase-locked-loop (PLL) filter. However, the adaptive filter may operate on an input signal without the use of a reference signal typically required by a conventional adaptive filter. The cost function of the adaptive filter may be represented by the equation as shown in Equation 1.

$$\min[y(n)-y(n-1)]^2 \qquad (1)$$

Furthermore, the adaptive algorithm implemented adjusts the oscillation signal w(n) at each step as shown in Equation 2 which states $$w(n+1) = 2\cos\left(2\pi\frac{f_0}{f_s}\right)w(n-1) - w(n-2) + \mu(y(n) - y(n-1)), \qquad (2)$$

where $\mu$ controls the step size and $\mu > 0$, $f_0$ is the notch frequency, $f_s$ is the sampling rate, and n is the sample index. Equations 1 and 2 explain how the adaptive algorithm may be implemented in a self-referencing adaptive notch filter.

For example, according to Eq. (1), the cost function is $\min[y(n)-y(n-1)]^2$ and the gradient of the cost function reflects the steepest ascent of the cost function. Thus, as y(n)=x(n)−w(n), the gradient of the cost function with respect to w(n) can be written in accordance with Equation 3 which states:

$$\frac{d[y(n) - y(n-1)]^2}{dw} = \frac{d[x(n) - w(n) - y(n-1)]^2}{dw} \qquad (3)$$

$$= -2[y(n) - y(n-1)]$$

In order to find the minimum of the cost function we need to take a step in the opposite direction of the gradient which is expressed mathematically as Equation 4 which states:

$$w(n+1) = w(n) + a\left(-\frac{d[y(n)-y(n-1)]^2}{dw}\right) \quad (4)$$

$$= w(n) + 2 \cdot a \cdot [y(n) - y(n-1)]$$

where a is the step size and a>0. Additionally, μ=2a and thus can be rewritten as Equation 5 which states:

$$w(n+1) = w(n) + \mu \cdot [y(n) - y(n-1)] \quad (5)$$

Moreover, when w(n)(estimated interference) is a pure sinusoid signal, it can be written as Equation 6 which states $$w(n) = A\sin\left(2\pi \frac{f_0}{f_s} n + \varphi\right), \quad (6)$$

where A is the amplitude, $f_0$ is the frequency, $f_s$ is the sampling rate, and φ is the phase. Thus, according to Eq. (4), w(n−1) and w(n−2) can be written as Equations 7 and 8, respectively, which state $$w(n-1) = A\sin\left(2\pi \frac{f_0}{f_s}(n-1) + \varphi\right) \quad (7)$$

$$w(n-2) = A\sin\left(2\pi \frac{f_0}{f_s}(n-2) + \varphi\right) \quad (8)$$

If $$\alpha = 2\pi \frac{f_0}{f_s}(n-1) + \varphi$$

and $$\beta = 2\pi \frac{f_0}{f_s},$$

then w(n), w(n−1), and w(n−2) can be written as Equations 9-11, respectively, as follows:

$$w(n) = A\sin\left(2\pi \frac{f_0}{f_s} n + \varphi\right) = A\sin(\alpha + \beta) \quad (9)$$

$$w(n-1) = A\sin\left(2\pi \frac{f_0}{f_s}(n-1) + \varphi\right) = A\sin(\alpha) \quad (10)$$

$$w(n-2) = A\sin\left(2\pi \frac{f_0}{f_s}(n-2) + \varphi\right) = A\sin(\alpha - \beta) \quad (11)$$

By using the following trigonometric identity of Equation 12, $$\sin(x) + \sin(y) = 2\sin\left(\frac{x+y}{2}\right)\cos\left(\frac{x-y}{2}\right) \quad (12)$$

the result is shown in Equation 13 which states $$w(n) + w(n-2) = 2A \sin(\alpha)\cos(\beta) = 2\cos(\beta)w(n-1). \quad (13)$$

And Equation 13 may be rewritten as follows in Equation 14

$$w(n) = 2\cos(\beta)w(n-1) - w(n-2) \quad (14)$$

$$= 2\cos\left(2\pi \frac{f_0}{f_s}\right)w(n-1) - w(n-2)$$

By replacing the value of w(n) in Eq. (5) with Eq. (14), the result is shown in Equation 15 which states $$w(n+1) = 2\cos\left(2\pi \frac{f_0}{f_s}\right)w(n-1) - w(n-2) + \mu(y(n) - y(n-1)). \quad (15)$$

Thus, as Equation (15) is equivalent to Equation (2), an adaptive algorithm may be implemented in a notch filter that does not include a reference signal, such as the one shown in FIG. 1.

While adaptive notch filters have had some success in estimating an amount of interference in an input signal to provide a filtered signal, these filtered signals often time have undesirable characteristics associated therewith resulting from less than optimal step size used by the notch filter. A system according to invention principles addresses deficiencies of known systems.

SUMMARY OF THE INVENTION

In one embodiment, a patient monitoring device that determines and monitors at least one patient parameter is provided. A configuration processor generates configuration information in response to a first input signal and an adaptive notch filter receives a second input signal. The second input signal includes a signal of interest and an interference signal in a predetermined frequency range. The adaptive notch filter automatically estimates the interference signal within the second input signal based on a filter parameter and removes the estimated interference signal from the second input signal to generate a target signal. A step processor is electrically coupled between the configuration processor and the adaptive notch filter and sets a value of the filter parameter based on the configuration information, wherein the adaptive notch filter uses the filter parameter to reduce a ringing artifact on the target signal below a threshold level.

In another embodiment, a method of removing an interference signal from an input signal in a patient monitoring device that determines and monitors at least one patient parameter is provided. The method includes the activities of generating configuration information in response to a first input signal and receiving a second input signal at an adaptive notch filter, the second input signal including a signal of interest and an interference signal in a predetermined frequency range. The adaptive notch filter automatically estimates the interference signal within the second input signal based on a filter parameter and removes the estimated interference signal from the second input signal to generate a target signal. The method includes setting a value of the filter parameter by a step processor electrically coupled between the configuration processor and the adaptive notch filter, the value of the filter parameter based on the configuration information and using the filter parameter to reduce a ringing artifact on the target signal below a threshold level.

BRIEF DESCRIPTION OF THE DRAWING FIGURES

FIG. 17 is a graph showing the results for settling time test;

FIG. 18 is a graph showing the results for recovery time test;

FIG. 19 is a graph showing the results for attenuation test;

FIG. 20 is a graph showing the results for square wave test;

FIG. 21 is a graph showing the results for saw wave test;

FIG. 22 is a graph showing the results for real interference test;

DETAILED DESCRIPTION

Figure 1:
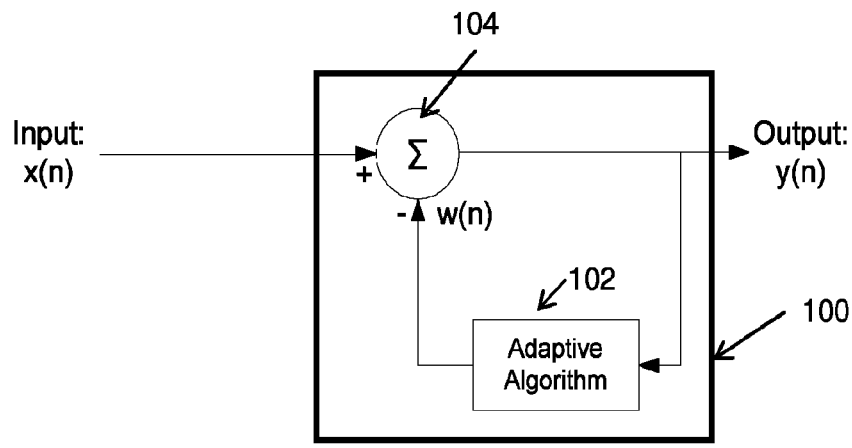
FIG. 1 is an exemplary block diagram of a prior art notch filter.

An adaptive notch filter advantageously improves removal of an amount of a particular type of interference from an input signal to produce a target signal. The input signal received by the adaptive notch filter includes a first signal component and a second signal component. The adaptive notch filter selectively filters one of the first component or the second component from the input signal in order to produce the target signal including the component of the input signal not filtered by the adaptive notch filter. Hereinafter, the first signal component will be used to describe the signal of interest and the second signal component will be used to refer to the external interference on the input signal. This is used for exemplary purposes only and one skilled in the art may recognize that the second signal component may include the signal of interest and the first signal component may include the interference. The first signal component represents the signal of interest and may be formed from a plurality of individual data samples. The second signal component represents the particular type of interference having a known frequency range associated therewith. In one embodiment, the interested signal may include interference caused by power line interference having a frequency of substantially 60 Hz. The notch frequency of the adaptive notch filter is set to a predetermined frequency range corresponding to the known frequency of the second signal component thus enabling removal of the second component from the input signal. The second component is removed in a known manner by an oscillator that oscillates at the notch frequency but in the opposite phase to remove the second signal component from the input signal to produce the target signal including only the first signal component.

The adaptive notch filter advantageously minimizes any ringing artifact resulting from attenuation of the input signal when removing the second signal component therefrom. The adaptive notch filter is responsive to configuration information associated with a characteristic of the input signal being filtered. The characteristic of the input signal may include any of (a) patient type from which the signal is derived; (b) amplitude of at least one respective sample of the signal of interest (e.g. first component); (c) a duration of respective samples of the signal of interest (e.g. first signal component); and (d) a change in duration of respective samples of the signal of interest. The configuration information may include a configuration parameter that controls how the adaptive notch filter operates to remove the interference from the input signal to produce the target signal. The configuration parameter advantageously enables adaptive filtering of an input signal by maximizing the convergence of the adaptive algorithm that controls notch filter operation in order to improve estimation and removal of the second signal component (e.g. interference) from the input signal. The configuration parameter further minimizes signal divergence that causes a ringing artifact in the target signal after removal of the interference from the input signal. In one embodiment, the configuration parameter is the step size associated with both the speed of algorithmic convergence and the amount of signal divergence. A larger step size results in quicker convergence but an increased divergence in the signal. In another embodiment, the configuration parameter includes a maximum absolute step size. The adaptive notch filter advantageously automatically and dynamically sets and modifies the configuration parameter in the configuration information in response to analyzing at least one sample of the target signal to maintain the configuration parameter at an optimal level. By continually analyzing samples within the processed target signals, the adaptive notch filter can be selectively controlled to maximize algorithmic convergence and minimize the ringing artifact associated therewith. Thus, the adaptive notch filter advantageously generates a cleaner signal that has less noise and is less perturbed due to the ringing artifact which allows for cleaner signal processing by a signal processing device.

Figure 2:
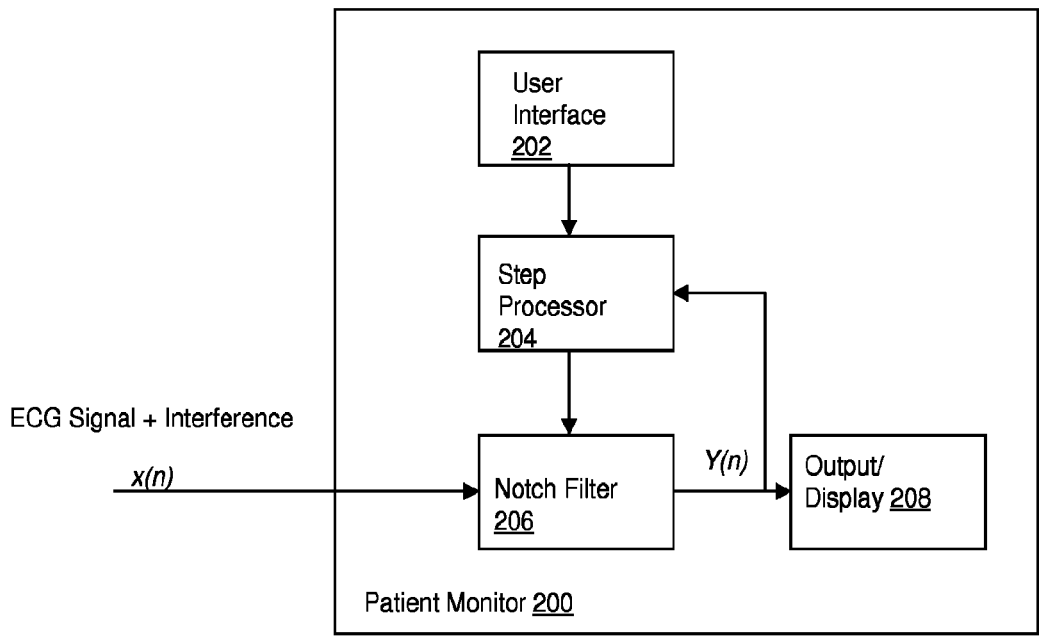
FIG. 2 is an exemplary block diagram of a patient monitor including the adaptive notch filter according to invention principles.

FIG. 2 is an exemplary block diagram of a patient monitor 200 including the adaptive notch filter according to invention principles. In this embodiment, the patient monitor is an electrocardiograph (ECG) monitor that is able to acquire electrical impulse data from at least one patient connected sensor (not shown). The patient monitor 200 includes a user interface 202, a step processor 204, the adaptive notch filter 206 and an output/display 208. One skilled in the art will appreciate that the patient monitor 200 will include other circuits and features that are needed for operation, however, these features will not be discussed as they are not necessarily germane to the present system. For example, the patient monitor will include a parameter processor or processing module that is able to execute at least one patient monitoring algorithm to derive patient parameter data from an input signal x(n) that include patient parameter data (e.g. ECG data) and at least some interference from an external source.

The user interface 202 is able to receive an input signal from a user that includes patient type information. The patient type information identifies at least on characteristic of the patient and is used to determine and operate the patient monitor 200 in a first mode associated with a first patient type or a second mode associated with a second different patient type. The patient type information is provided to the step processor 204 which determines, based on the patient type information, a maximum step value to be implemented by the adaptive algorithm of the adaptive notch filter 206. Each of the first and second modes of operation have different maximum step size values associated therewith. Upon determining the maximum step value, the step processor 204 conditions the adaptive notch filter 206 to implement the determined maximum step value on any input signals x(n) processed thereby. In an alternative embodiment the step processor may receive or otherwise obtain patient type information from an external source of patient information. This may be received at predetermined or random time intervals in order to ensure the maximum step value applied by the adaptive notch filter is correct for the type of patient being monitored.

Once the operational mode is determined using the patient type information resulting in the respective maximum step value associated with the determined operational mode being set, the adaptive notch filter 206 selectively and automatically uses the maximum step value for estimating and removing an amount of interference from the input signal x(n). In exemplary operation, the patient monitor 200 may receive at least one input signal x(n) that includes ECG data obtained from ECG leads attached to a patient (not shown). This input signal also includes interference that is derived from an external source such as power line interference which is sinusoidal in nature and has a known frequency associated therewith. The input signal x(n) is filtered by the adaptive notch filter 206 in a known manner using an adaptive algorithm that includes a set size value equal to the maximum step value set by the step processor 204. This produces an output (e.g. target) signal y(n) that includes only an interested signal that may be used to determine and monitor the particular patient parameter by other know patient parameter processing circuits (not shown) in a known manner. In this embodiment, the interested signal includes unprocessed ECG signal data. In response to setting the maximum step size used in the adaptive algorithm implemented by the notch filter 206 based on a patient type, a ringing artifact on the output signal y(n) is minimized below a threshold level. The output signal y(n) may be processed to determine and monitor data in a known manner by additional circuitry and provided to the output/display 208 enabling a user to view or monitor the modified ECG signal. As shown herein, the output/display is formed integral with the patient monitor. However, the output/display may be remotely located from the patient monitor. Alternatively, the output may be communicated via a communication network for storage in a source of patient information.

In an another embodiment, as will be discussed in greater detail hereinafter with respect to FIG. 4, the step processor 204 may automatically and dynamically modify the value of the maximum step size in response to at least one monitoring condition monitored by the patient monitor 200. The output signal y(n) including the interested signal is processed to generate patient parameter data and the patient monitor is able to selectively analyze at least one characteristic of the patient parameter data (e.g. ECG data) and automatically recalculate the maximum step value set by the step processor 204 and implemented by the adaptive notch filter 206 based on the characteristics associated with the patient parameter data. In the embodiment where the patient monitor 200 is an ECG monitor, the characteristics may include any characteristic associated with respective QRS values in the ECG data or any other waveform values able to be derived from the ECG data. This feedback advantageously ensures that the maximum step value for the adaptive notch filter will minimize the ringing problem of any input signal even when the patient monitor is set to operate in one mode but the patient parameter data being monitored suggests that a filtering parameter associated with a different operational mode should be employed at a given time. This advantageously enables the patient monitoring device to remain configured according to the original operational mode but modifies a parameter used in filtering the input signal thereby affecting a subset of monitoring parameters and minimizing any ringing artifact associated therewith.

Figure 3:
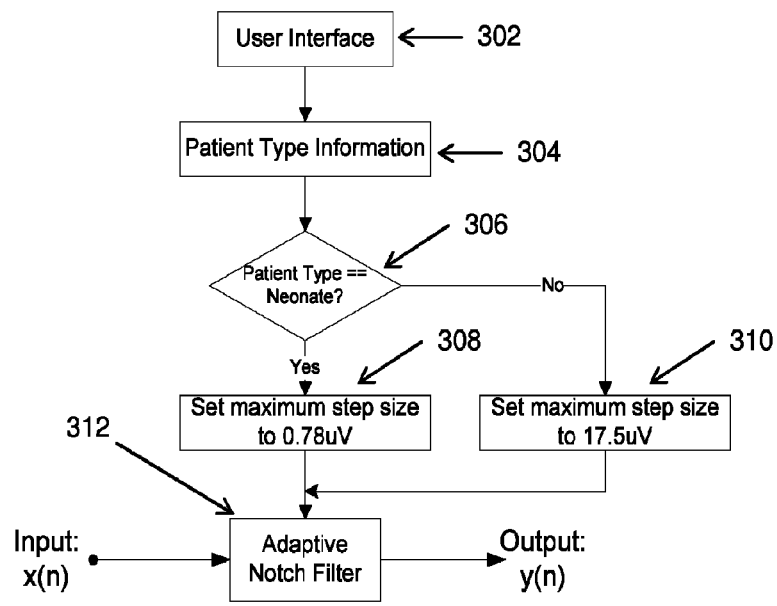
FIG. 3 is a flow diagram detailing the operation of a patient monitor including the adaptive notch filter.

The operation of the exemplary patient monitor 200 including the patient-type controlled adaptive notch filter described in FIG. 2 is represented by the flow diagram of FIG. 3. At block 302, a user may engage a user interface to enter data representing patient type information in block 304. Patient type information may include the type of patient and at least one characteristic associated with the patient. Alternatively, the patient type information may be automatically acquired from a remote source of patient information via a communications network at predefined intervals. In one embodiment, a characteristic associated with the patient and included in the patient type information identifies whether or not a particular patient is a neonatal patient or a non-neonatal patient (e.g. adult or pediatric patient). Upon receipt of the data representing the patient type information, the patient monitor, in block 306, determines if the patient is a neonatal patient. If the patient is determined to be a neonatal patient, the step processor (204 in FIG. 2) conditions the adaptive notch filter to implement a first maximum step size for the adaptive algorithm that is optimally associated with a neonatal patient in block 308. In an exemplary embodiment, the first maximum step size is substantially 0.78 microvolts (uV). If the determination in block 306 is negative indicating that the patient is not a neonatal patient, the step processor (204 in FIG. 2) conditions the adaptive notch filter to implement a second maximum step size for the adaptive algorithm that is optimally associated with a non-neonatal patient in block 310. In an exemplary embodiment, the first maximum step size is substantially 17.5 microvolts (uV). Upon setting the maximum step value of the adaptive notch filter as one of the first maximum step size or the second maximum step size based on the determination in block 306, the adaptive notch filter executes the adaptive algorithm to estimate and filter an input signal x(n) that includes the interested signal (e.g. first component) and interference (e.g. second component) in block 312. The input signal x(n) is filtered by the adaptive notch filter in block 312 to produce a target output signal y(n) that includes the interested signal and which removes the interference therefrom in a known manner. By setting the maximum step size used by the adaptive notch filter based on the type of patient, the adaptive notch filter advantageously minimizes and/or otherwise corrects any ringing artifact present in the target signal once the interference is removed from the original input signal x(n).

Figure 4:
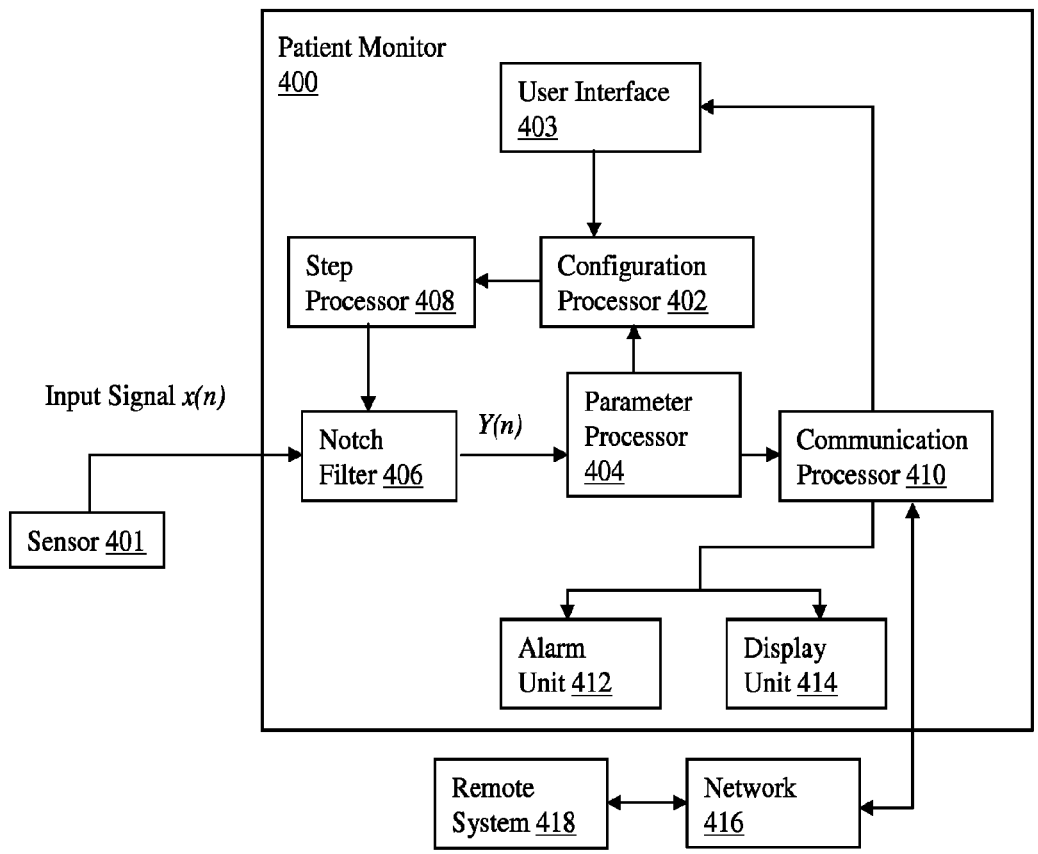
FIG. 4 is an exemplary block diagram of a patient monitor including the adaptive notch filter according to invention principles.

Another exemplary embodiment of a patient monitor 400 is shown in FIG. 4. FIG. 4 provides an embodiment of the patient monitor 400 showing certain additional components that, while described in FIG. 2, were not explicitly shown therein. One skilled in the art would understand that the embodiments in FIGS. 2 and 4 may be readily combined.

The patient monitoring device 400 includes a configuration processor 402 that selectively controls an operational mode of the patient monitoring device 400. The configuration processor 402 is able to control the patient monitoring device to operate in one of at least two predetermined operating modes. The respective operating modes controlled by the configuration processor 402 each include a plurality of operational mode-specific monitoring settings that enable the patient monitoring device 400 to acquire, process, analyze and monitor data from a particular patient to which the patient monitoring device is connected. The configuration processor 402 may control the patient monitoring device to operate in a first mode associated with a first type of patient using a first set of monitoring settings to determine and monitor a particular type of patient parameter data. The configuration processor 402 may also control the patient monitoring device 400 to operate in a second mode associated with a second different type of patient using a second set of monitoring settings to determine and monitor the particular patient parameter data. The patient monitoring device 400 may include a user interface 403 electrically coupled to the configuration processor 402. The user interface 403 is selectively configured to receive an input from a user that selectively configures the patient monitor 400 to operate in one of the first mode associated with the first type of patient or the second mode associated with the second type of patient. In one embodiment, the first type of patient is a neonatal patient, and upon identifying the patient as a neonatal patient via the user interface 403, the configuration processor 402 automatically controls the patient monitor to implement neonatal specific patient monitoring settings used to derive and monitor the at least one patient parameter. In this embodiment, the second type of patient is a non-neonatal patient (e.g. pediatric or adult patient). Upon identifying that the patient is not a neonatal patient via the user interface 403, the configuration processor 402 automatically controls the patient monitor to implement non-neonatal specific patient monitoring settings used to derive and monitor the at least one patient parameter. Prior to initial operation, the patient monitoring device 400 needs to be configured to operate in either the first mode or the second mode and this configuration is generally done using the user interface 403.

A parameter processor 404 is electrically coupled to the configuration processor 402 and is controlled thereby to process data derived from at least one patient connected sensor 401. While only a single sensor 401 is shown herein, persons skilled in the art will appreciate that any number of sensors 401 may be coupled to the patient monitoring device 400 depending on the type of patient parameter being monitored thereby. The parameter processor 404 receives data representing the monitoring settings associated with the particular type of operational mode identified by the configuration processor 402. In response to data representing the monitoring settings, the parameter processor 404 executes at least one parameter monitoring algorithm that enables data derived from the at least one sensor 401 to be processed and transformed into patient parameter data that allows a healthcare professional to monitor the particular patient parameter.

Data sensed by the at least one sensor 401 represents a first component of the input signal x(n) that is provided to the patient monitoring device 400. However, as is well known, in healthcare environments, additional external interference that negatively impacts the ability of the patient monitoring device 400 to derive and monitor patient parameter data is prevalent. The external interference is also present in the input signal x(n) and represents a second signal component therein. In order to effectively determine the patient parameter data using the first signal component, the patient monitoring device 400 includes an adaptive notch filter 406. The adaptive notch filter 406 operates in a known manner in accordance with an adaptive filtering algorithm that continually and automatically estimates the value of the second component of the input signal x(n) and filters the second component from the input signal x(n) to generate the target signal y(n) that includes only the data sensed from the patient which is used to determine and monitor the at least one patient parameter.

However, as noted above, based on the type of patient to which the at least one sensor 401 is connected, certain filter parameters may be selectively modified in order to produce a cleaner target signal y(n). As used herein, the term cleaner target signal represents a signal having the second component representing external interference filtered out while minimizing the presence of the ringing artifact in the target signal. A step processor 408 that is electrically coupled between the notch filter 406 and the configuration processor 402 selectively controls, sets and/or modifies the filter parameter to produce the clean target signal y(n). In one embodiment, the filter parameter may represent a maximum absolute step size used in the adaptive algorithm that estimates and removes an amount of interference from the input signal x(n). The step processor 408 configures the filter parameter of the notch filter 406 in response to configuration information received from the configuration processor 402. The configuration information may be determined by the configuration processor 402 via (a) user input of patient type via the user interface 403 to identify an initial setup of the patient monitoring device 400 or (b) feedback analysis of the at least one patient parameter data generated by the parameter processor 404. The step processor 408 configures the notch filter 406 to operate using a first filter parameter when the patient monitor 400 is operating in the first mode and a second different filter parameter when the patient monitor is operating in the second mode. In one embodiment, the first filter parameter represents a step size in microvolts that is less than the second filter parameter. For example, the first filter parameter may be a maximum step size of substantially 0.78 uV and the second filter parameter may be a maximum step size of substantially 17.5 uV.

The determination of configuration information based on a feedback analysis of the at least one patient parameter will now be discussed. Using a feedback analysis to selectively set and/or modify the filter parameter used by the adaptive notch filter advantageously enables a quick and automatic response to a change detected in the patient parameter derived from the interested signal of the input x(n). This further advantageously allows for reconfiguration of a set of monitoring settings being used by the patient monitor 400 without fully reconfiguring the patient monitor. This may occur, for example, when despite the patient being identified as one of the first or second type of patient, the patient parameter data determined by the parameter processor 404 exhibits a characteristic that is typically associated with a patient type for which the patient monitor is not configured.

After the at least one patient parameter is determined using data contained in target signal y(n), the configuration processor 402 automatically analyzes at least one characteristic associated with the patient parameter data to determine if the patient parameter data is exhibiting a characteristic that is typically not associated with the patient type that the patient monitor 400 is configured to monitor. The analyzed characteristic of the patient parameter data is compared to a known range of acceptable characteristics for the particular patient type and, if the configuration processor 402 determines that the characteristics fall within the accepted range, then configuration processor 402 takes no action and the patient monitor 400 remains in the current operating mode using the specified filter parameter. If the characteristic of the patient parameter data is determined to be outside the accepted range for the particular type of patient, the configuration processor 402 automatically compares the characteristic of the patient parameter data with accepted ranges for other patient types to determine if the determined patient parameter data is representative of a different patient type. Upon identifying which patient type the characteristic matches, the configuration processor 402 automatically checks to if the filter parameter for that particular patient type matches a current filter parameter value. If so, the configuration processor 402 takes no action and maintains the current operational mode using the current filter parameter. Upon determining that the filter parameter should be different based on the detected characteristic, the configuration processor 402 automatically causes the step processor 408 to modify only the filter parameter being used by the notch filter 406 while maintaining the previously identified operational mode. By only modifying the filter parameter, the configuration processor 402 ensures that no other monitoring settings associated with the specified patient type are changed. Additionally, the characteristic of the at least one patient parameter is generally associated with one of the particular patient types set by the user. However, there are instances when the characteristic of one patient type may be seen in the patient parameter data determined for the other patient type. Thus, automatic modification of the filter parameter to improve estimation and removal of interference as well as minimize ringing artifacts on the signal from which the interference has been removed, advantageously ensures that the at least one patient parameter being determined by the patient monitor 400 is based on a clean signal using only data sensed from the particular patient.

The characteristic analysis performed by the configuration processor may be performed at least one of (a) continually; (b) at a predetermined time interval; (c) over a predetermined time interval; (d) in response to user command; and (e) in response to the patient parameter data falling below or exceeding a threshold level.

A communication processor 410 may also be selectively coupled to each of the parameter processor 404 and user interface 403. The parameter processor 404 may generate communication control signals that control the communication processor 410 to selectively communicate patient parameter data to at least one of a display unit 414, an alarm unit 412 and a remote computing system 418 via a communications network 416. The data communicated by the communication processor 410 may include any data sensed or derived by the parameter processor 404. The communication processor 410 may also selectively receive command data from one of (a) a user of the remote system or (b) the remote system itself via the network 416. The command data received by the communication processor may be selectively provided to the user interface 403 and used by the configuration processor 402 to generate configuration information that enables control and operation of the patient monitoring device. This advantageously enables remote configuration of the patient monitor 400 based on the patient type selected by a remote user.

Additionally, the communication processor 410 enables a further parameter change confirmation feature in the embodiment wherein the filter parameter is automatically modified in response to an analysis of at least one characteristic of the determined patient parameter data. Upon determining that the characteristic of the determined patient parameter requires a change of the filter parameter implemented by the notch filter 406, a filter parameter change message is provided to the communication processor 410. The communication processor 410 may communicate the filter parameter change message to the remote system 418 (or user thereof, e.g. a central monitoring station) via the network 416. This advantageously notifies a healthcare professional that the current filter parameter is being updated to an updated filter parameter typically associated with a different type of patient than the patient monitor 400 is configured to monitor and request confirmation that the patient type has not changed. The filter parameter, despite being automatically changed by the step processor 408, may be reverted back to the original filter parameter if a user that receives the change message indicates that the change has occurred in error. In another embodiment, receipt of the filter parameter change message may also spur the healthcare profession to perform a clinical action on behalf of the patient to determine why the characteristic of the patient parameter has changed. In another embodiment, the message may also be communicated via the network 416 and received by the remote system such that this message is stored in a repository of patient history information. This advantageously enables the healthcare enterprise to fully chronicle all patient activity. In one embodiment, parameter data and filter parameter data may be selectively communicated at least one of (a) simultaneously; (b) sequentially; (c) in response to the parameter processor 404 determining that a value of the characteristic of the patient parameter data has reached, exceeded, or fallen below a threshold value; or (d) in response to receipt of an external request (user generated or automatically generated by a computing system) requesting transmission of the patient parameter or filter parameter data. The communication processor 410 may also be able to selectively receive control requests from remote computing systems 418 (or users thereof) that selectively modify the operation of the apparatus. In a further embodiment, the patient parameter processor 404 may automatically and in real-time compare characteristics of the patient parameter data to threshold characteristic values and, if the characteristics of the patient parameter data at least one of (a) equals a threshold; (b) exceeds a threshold; and (c) falls below a threshold. The patient parameter processor 404 may selectively control the communication processor 410 to signal at least one of the display unit 412 or alarm unit 414 to notify a healthcare professional that the patient may require a clinical or other action be taken on their behalf.

Figure 5:
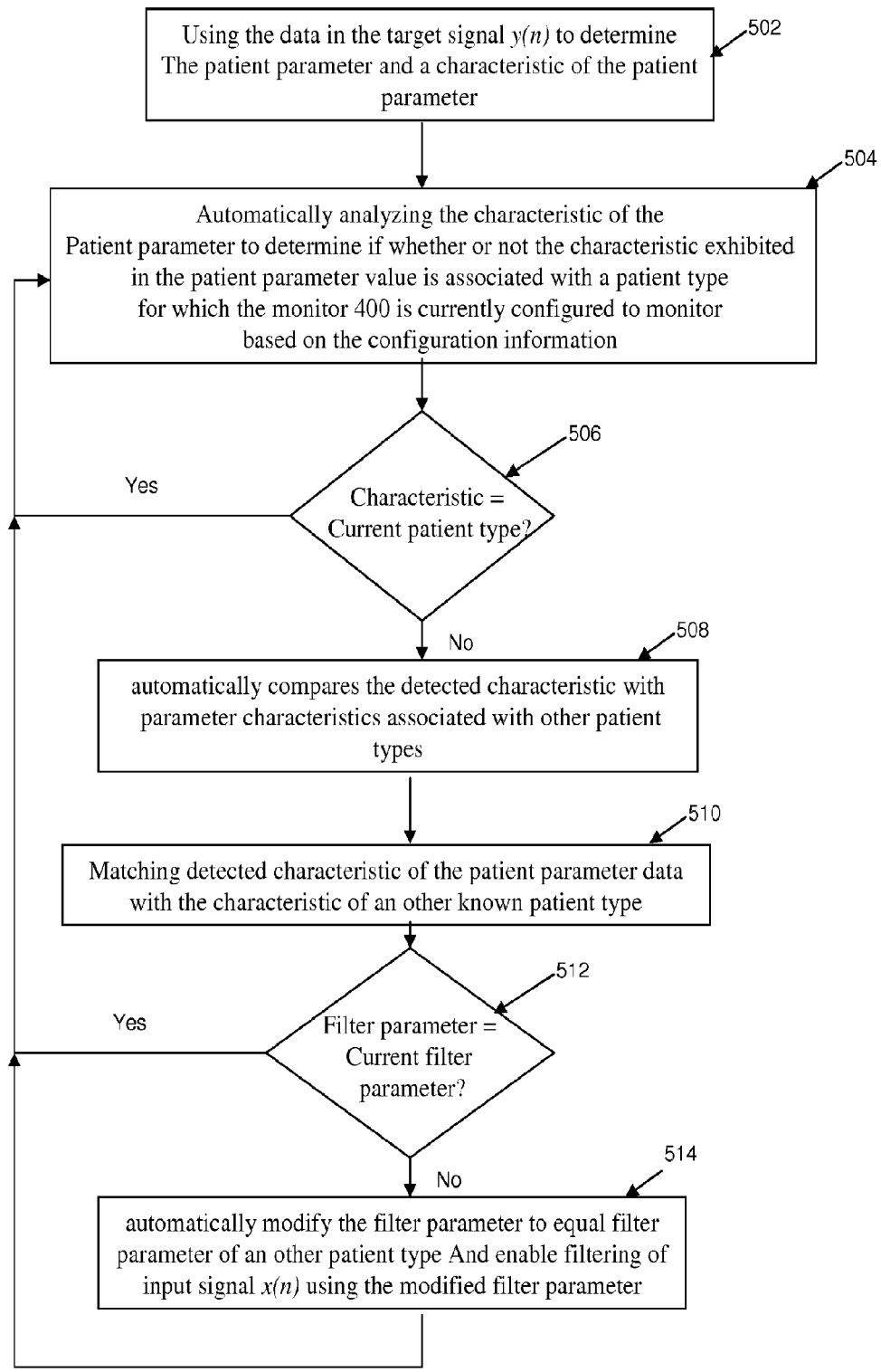
FIG. 5 is a flow diagram detailing the operation of a patient monitor including the adaptive notch filter.

The patient monitor 400 described with respect to FIG. 4 may operate in accordance with the blocks in the flow diagram of FIG. 3. In this manner of operation, the initial configuration of the patient monitor 400 based on the type of patient is described. Exemplary operation of the patient monitor 400 including the feedback analysis described in FIG. 4 is shown in the flow diagram of FIG. 5.

In block 502, the target signal y(n) is used to determine at least one patient parameter having at least one characteristic associated therewith. In block 504, the configuration processor 402 may automatically analyze the characteristic of the determined patient parameter to determine whether or not the characteristic exhibited by the patient parameter value is associated with a patient type for which the monitor 400 is currently configured based on the configuration information provided via the user interface 403. A determination is made in block 506 as to whether or not the characteristic detected in the patient parameter data is associated with the current patient type configuration. If the determination in block 506 is positive indicating that the characteristic is associated with the current patient type, then no action is taken and operation reverts back to block 504. If the determination in block 506 is negative, the configuration processor 402 automatically compares the detected characteristic with parameter characteristics associated with other patient types in block 508. The detected characteristic of the patient parameter data is matched with the characteristic of other known patient types in block 510. Upon indentifying with which patient type the detected characteristic is associated, the configuration processor 402 automatically determines if the filter parameter value for the other patient type is equal to the current filter parameter type associated with the current patient type in block 512. If the current filter parameter is determined to be equal to the filter parameter of the other patient type, then no action is taken and operation reverts back to block 504. If the determination in block 512 is negative, then the configuration processor 402 automatically controls the step processor 408 to modify the filter parameter value being used by the adaptive algorithm of the notch filter 406 and the notch filter begins filtering the immediate samples of the input signal x(n) using the modified filter parameter. Operation then reverts back to block 504 to continually and automatically determine if and when the filter parameter should be modified based on the characteristic of the patient parameter as determined by the parameter processor 404. In another embodiment, distortion in the signal maybe compensated for by removing only the power line interference using a smaller frequency of interest in the adaptive notch filter.

In one embodiment, the patient monitoring device 400 is an electrocardiograph (ECG) monitor that selectively determines ECG data for the patient connected thereto. While specific reference will be made to components shown in FIG. 4, persons skilled in the art will appreciate that the embodiment represented in FIG. 2 may also operate in a similar manner. In this embodiment, the configuration processor 402 may control the patient monitor 400 to operate in a particular operational mode in response to user input received via the user interface 403.

A user may selectively configure the ECG monitor 400 to operate in a first operational mode when the patient type is identified as (or determined to be) a neonatal patient. When operating in the first mode, the configuration processor 402 causes the patient to monitor the neonatal patient using a plurality of neonatal patient specific monitoring settings in order to determine and monitor ECG data for the neonatal patient. A user may also selective configure the ECG monitor 400 to operate in a second operational mode when the patient type is identified as (or determined to be) a non-neonatal patient (e.g. pediatric or adult patient). When operating in the second mode, the configuration processor 402 causes the patient monitor to monitor the non-neonatal patient using a plurality of pediatric/adult-specific monitoring settings in order to determine and monitor ECG data for non-neonatal patients. The two operational modes are important because certain characteristics of ECG data associated with a neonatal patient are different from the characteristic of ECG data associated with non-neonatal patients. For example, the characteristic may include QRS complex duration and, in a neonatal patient, the QRS complex typically has a duration of substantially between 15 milliseconds and 20 milliseconds whereas the QRS duration for adult or pediatric patients is substantially between 70 milliseconds and 100 milliseconds. The QRS complex duration of a neonatal patient is substantially smaller than the QRS complex duration of a non-neonatal patient. Thus, when an input signal x(n) is presented at an input to a notch filter charged with removing external interference from the input signal to leave only the signal of interest, the notch filter may have difficulty effectively estimating and removing the external interference due to the interested signal appearing as an impulse. To remedy this, the step size utilized by the adaptive algorithm controlling notch filter operation is changed based on the selected mode of operation.

Upon configuring the patient monitor to operate in the first mode of operation, the configuration processor 402 causes the step processor 408 to set a value for the maximum step size of the adaptive algorithm to be equal to a first maximum step size value. In one embodiment, the first maximum step size is substantially 0.78 uV. By automatically setting the step size to the first maximum step size value, the notch filter 406 is able to effectively remove the external interference without a ringing artifact resulting on the target signal of interest y(n). The target signal of interest is then provided to the parameter processor 404, which, in this embodiment, is an ECG processor able to detect QRS complexes and generate ECG data from the samples contained in the target signal of interest y(n) using neonatal-specific parameter detection algorithms.

If the patient monitor is configured to operate in the second mode of operation, the configuration processor 402 causes the step processor 408 to set a value for the maximum step size of the adaptive algorithm to be equal to a second maximum step size value, the second maximum step size value being greater than the first maximum step size value. In one embodiment, the second maximum step size is substantially 17.5 uV. By automatically setting the step size to the second maximum step size value, the notch filter 406 is able to effectively remove the external interference without a ringing artifact resulting on the target signal of interest y(n). The target signal of interest is then provided to the ECG processor 404, to detect QRS complexes and generate ECG data from the samples contained in the target signal of interest y(n) using non-neonatal specific parameter detection algorithms.

Figure 6:
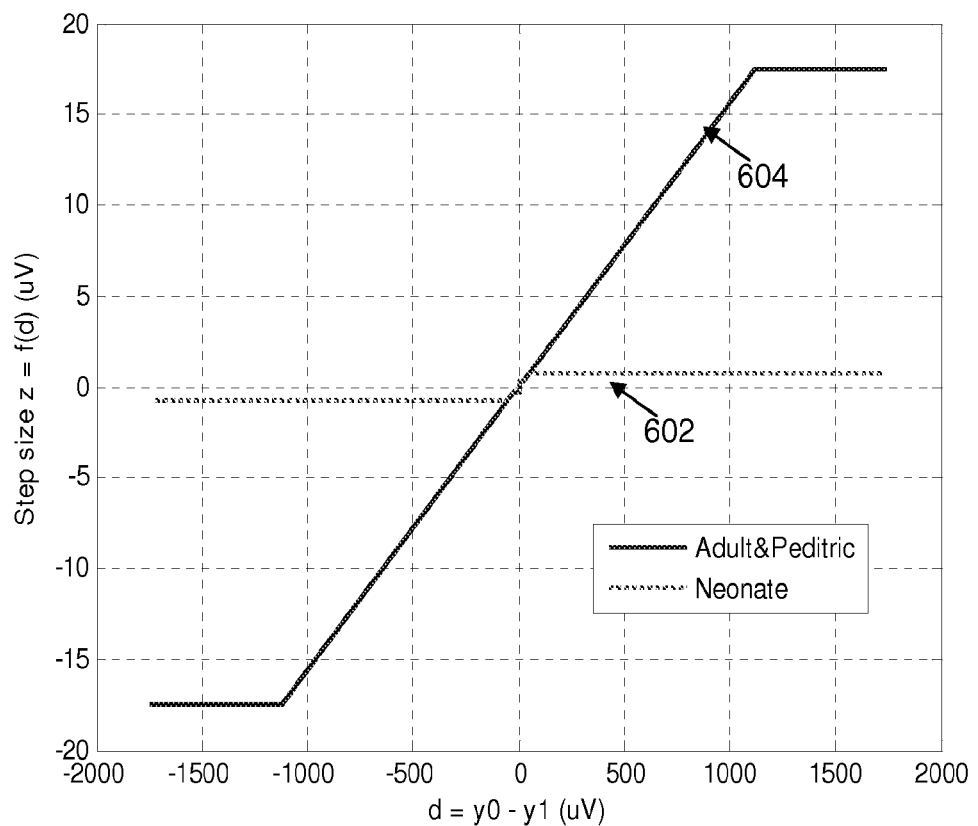
FIG. 6 is a graph showing the relationship between the Neonatal and non-neonatal step size.

A graphic representation of the first filter parameter having a first maximum step size and the second filter parameter having the second maximum step size is shown in FIG. 6. FIG. 6 represents the relationship between the estimation error d on the x axis and step size z on the y axis. The plot labeled with reference number 602 represents the first filter parameter where the maximum step size is 0.78 uV and the plot labeled with reference number 604 represents the second filter parameter where the maximum step size is 17.5 uV. It is important to note that as used herein, maximum step size values are absolute values. Thus, FIG. 6 shows that the first filter parameter is substantially smaller than the second filter parameter in order to compensate for the specific characteristics associated with neonatal ECG data.

In another embodiment, the ECG monitor automatically analyses the characteristic of the ECG data in order to determine if the current filter parameter is the optimal filter parameter. The analysis of ECG characteristics may occur continually, at predetermined time intervals or in response to user command to perform the analysis. Additionally, the analysis may include analyzing ECG data on a sample by sample basis or using a discrete set of ECG data samples over a predetermined time period and performing a statistical analysis thereon to determine a value for the characteristic over the predetermined time period. For purposes of example and ease of understanding, the following discussion of the operation will reflect analysis of individual samples of ECG data. The characteristic analysis performed by the configuration processor 402, identifies duration of the QRS complex previously determined by the ECG processor and compares the identified QRS complex duration with a threshold range of QRS complex duration values known to be associated with the patient type for which the ECG monitor 400 is configured to monitor. If the identified QRS complex duration is within the threshold range of QRS complex duration values, the ECG monitor 400 continues to operate using its current configuration information and the notch filter 406 uses the currently set filter parameter (e.g. maximum step size) in the adaptive algorithm that estimates and filters external interference from an input signal x(n).

If the identified QRS complex duration value is outside of the threshold range of QRS complex duration values, the configuration processor 402 conditions the step processor 408 to automatically modify the filter parameter value (e.g. maximum step size) to be equal to the filter parameter value for the patient type for which the ECG monitor is not configured. For example, if the ECG monitor is configured to operate in the second mode to monitor a non-neonatal patient, the configuration processor 402 conditions the step processor 408 to set the maximum step size equal to the second maximum step size value because the QRS complex duration associated with a non-neonatal patient is known to be within a first range of known QRS complex durations (e.g. 70 ms-100 ms). If, during the course of patient monitoring, the configuration processor 402 analyzes the ECG data and determines that the duration of the QRS complex is outside of the known range (e.g. below the range for non-neonatal patients and within a range typically associated with neonatal patients), the configuration processor 402 conditions the step processor 408 to automatically modify the filter parameter of maximum step size to be equal to the first maximum step size. The step processor 408 automatically causes the notch filter to operate using the first maximum step size. By only changing the filter parameter, the remaining monitoring settings associated with the type of patient set upon initialization of the ECG monitor advantageously remains the same. The characteristic analysis may be continual to ensure that the filter parameter that controls a portion of the operation of the adaptive notch filter 406 optimally estimates and filters external interference of a known frequency from an input signal in order to produce a target signal of interest that minimizes any ringing artifact associated therewith.

Figure 7A:
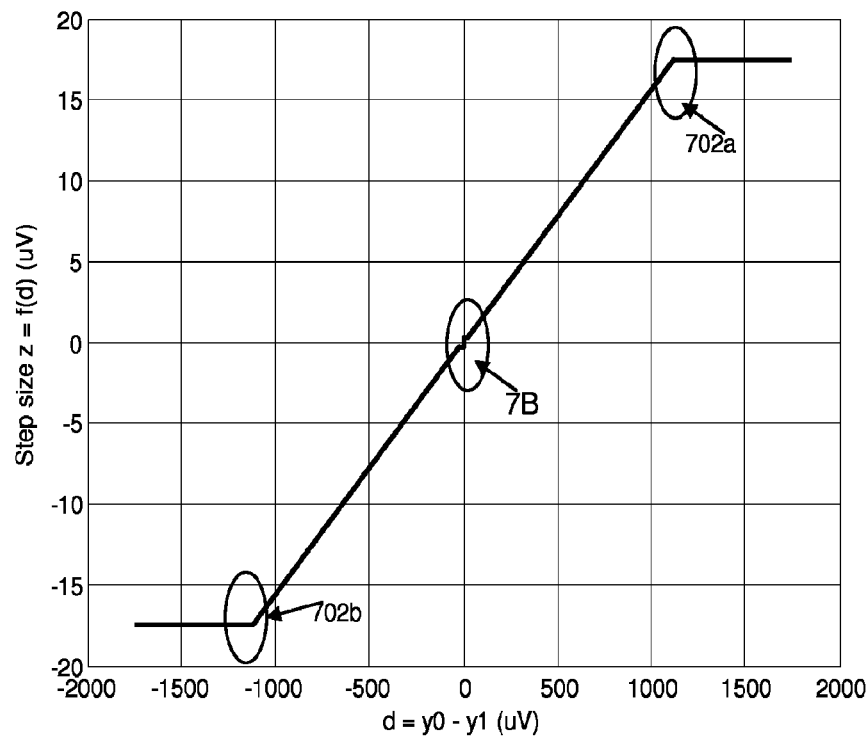
FIG. 7 is a graph showing the relationship between step size z and estimation error d.
Figure 7B:
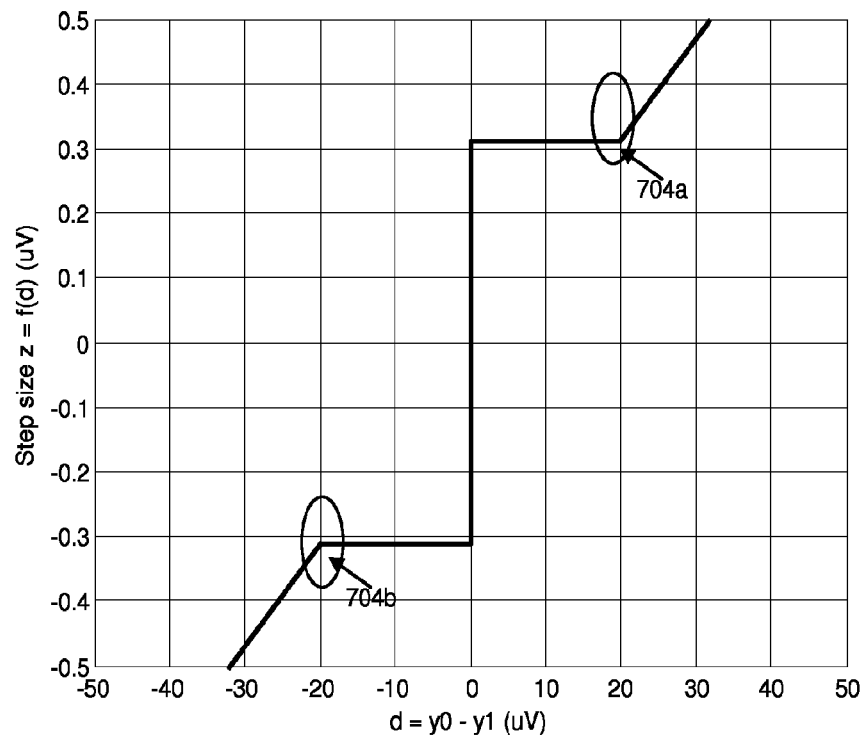

The following discussion of FIGS. 7-25 describe the advantages presented by configuring at least one filter parameter used by the adaptive notch filter according to the type of patient being monitored by the monitoring device. As discussed above, the value of the first and second filter parameters (e.g. step size) is critical to the convergence of an adaptive algorithm. According to Eq. (2), the value of the step size is $\mu(y(n)-y(n-1))$ and upper and lower bounds may be applied to the step size to avoid divergence. An example of the step size function is shown in FIGS. 7A and 7B. FIGS. 7A and 7B represent the relationship between the step size value (z) and interference estimation error d of respective samples of input signal x(n). FIG. 7A is an overall view of exemplary upper and lower bounds applied to the step size used by the adaptive notch filter 406. The upper bounds of the maximum step size are shown in the circle labeled 702a which is substantially +17.5 uV and in the circle labeled 702b which is −17.5 uV. There are positive and negative maximum step size values due to the positive and negative peak to peak in the ECG signal for which compensation is needed. Thus, the filter parameter described above is represented in terms of absolute value. Therefore, FIG. 7A shows that the maximum absolute step size is limited to 17.5 uV. FIG. 7A also shown the minimum absolute step size (e.g. noise floor of the filter) in the circle labeled 702c which is shown, in an expanded view, in FIG. 7B. In FIG. 7B, the minimum absolute step size is shown in the circles labeled 704a which is substantially +0.3125 uV and in the circle labeled 704b which is −0.3125 uV. Thus, the minimum absolute step size used by the adaptive notch filter 406 is limited to 0.3125 uV. FIG. 7B indicates that even when the estimation error d is zero, the step size z is not zero. Rather, the step size is either +0.3125 uV or −0.3125 uV, so the noise floor in the output y(n) can never be zero to avoid a lock-up situation whereby the filter is stuck and is unable to release from a certain state.

Figure 8A:
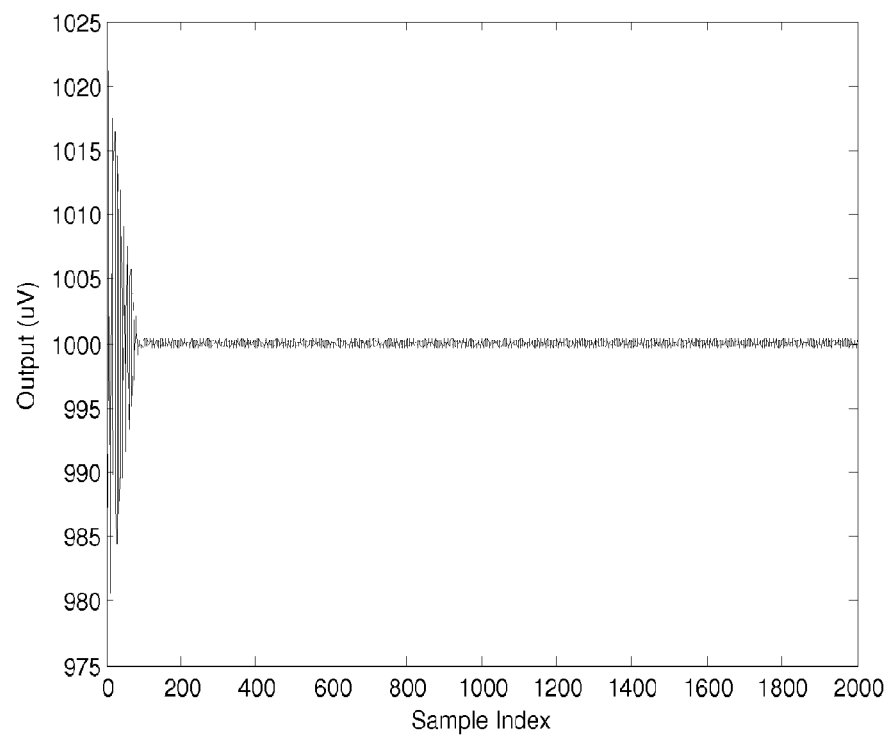
FIG. 8 is a graph showing the output of a notch filter when the input is a 1 mV DC signal.
Figure 8B:
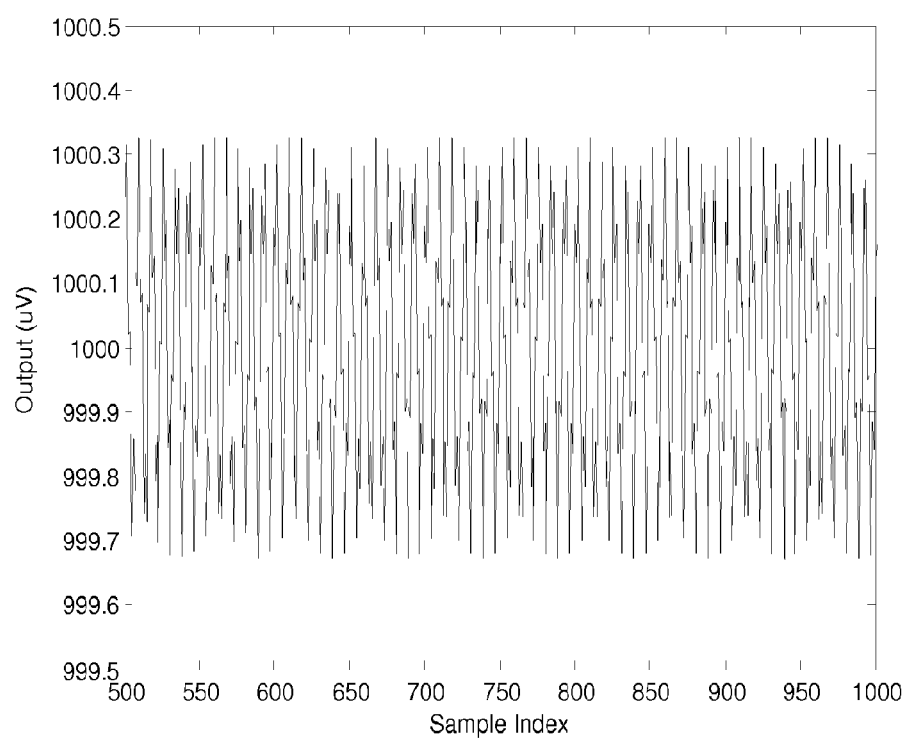

FIGS. 8A and 8B and 9A and 9B graphically represent that the lower bound of the step size (e.g. minimum step size) determines the noise floor of the notch filter 406. FIGS. 8A and 8B are graphical representations showing the relationship of the output of an exemplary notch filter 406 in microvolts and the perturbations in respective samples in the output signal. FIGS. 8A and 8B show the notch filter output when the input to the notch filter is a 1 mV DC signal. Further, the notch frequency of the notch filter was set to 60 Hz which substantially mirrors the known frequency of power line interference sought to be removed from the input signal. It can be seen in FIG. 8A that, once the output signal is stabilized, the peak to peak perturbation of the output signal is at a substantially ideal level. In this case, when the input is a 1 mV DC signal, the perturbation as shown in the expanded view in FIG. 8B is substantially ±0.3125 uV, which is the lower bound of the step size.

Figure 9A:
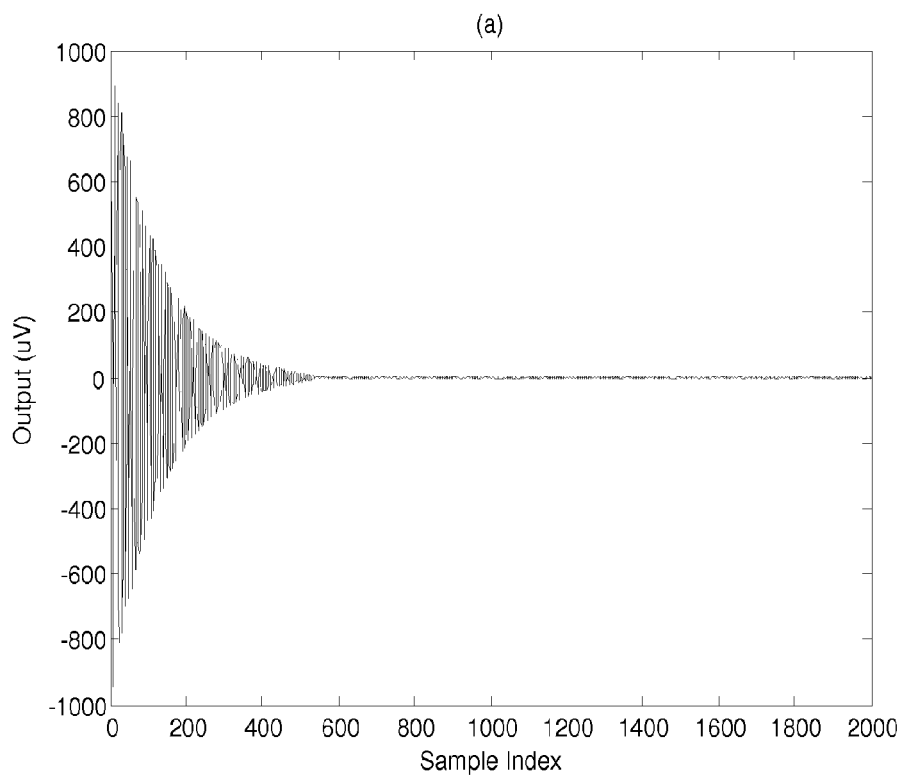
FIG. 9 is a graph showing the output of the notch filter when the input is a pure sinusoid signal.
Figure 9B:
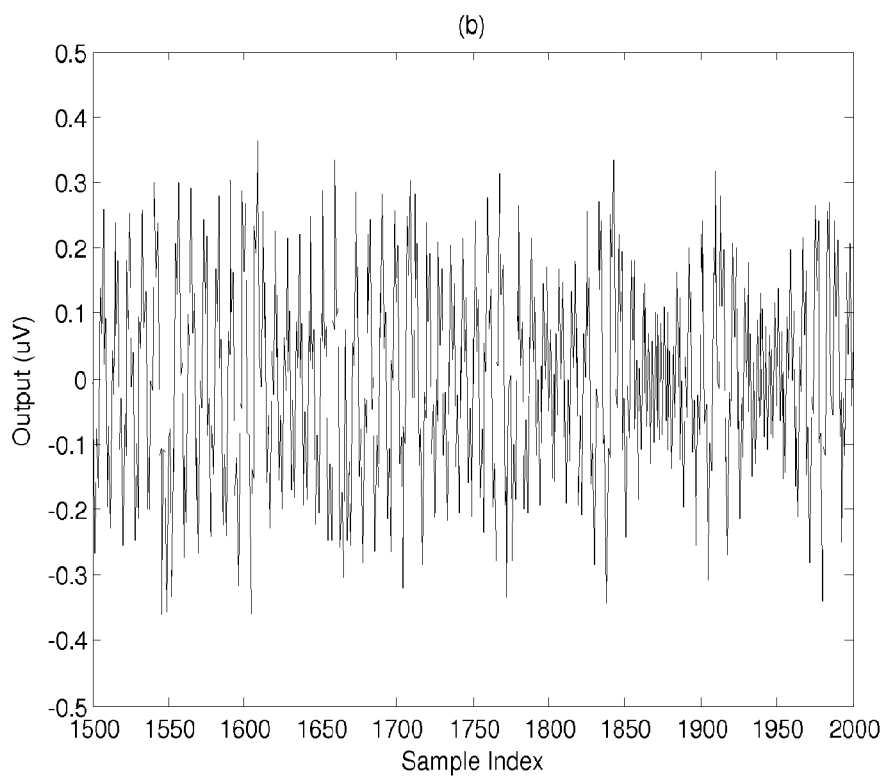

FIGS. 9A and 9B are graphical representations of the output of the notch filter output when the input signal was a pure sinusoid with a frequency at 60 Hz and having an amplitude of substantially 1 mV. In this test, the notch frequency of the filter is set to 60 Hz and the sampling rate is 500 Hz. It can be seen that the sinusoid input signal (e.g. power line interference) is successfully removed from the output after 500 samples or 1 millisecond. Once removed, the residual perturbation is substantially ±0.3125 uV as can be seen in FIG. 9B which is the lower bound of the step size. Thus, from FIGS. 8 and 9, one skilled in the art would understand that the lower bound (e g minimum step size) determines the noise floor of the notch filter.

Figure 12:
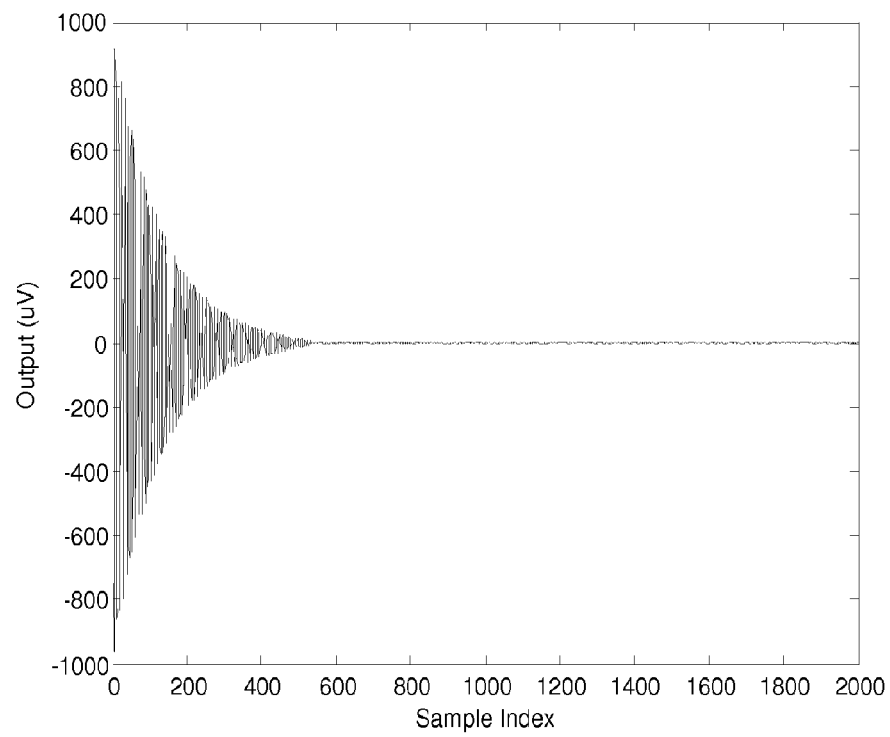
FIG. 12 is a graph showing the output of the notch filter having an upper bound value set at 17.5 uV when the input is a pure sinusoid signal.

FIGS. 10-12 are graphical representations showing the importance of the proper maximum step size selected for use by the adaptive notch filter. The upper bound represents the maximum step size limit Referring back to FIG. 7A, when the estimation error d is larger than 1.12 mV, the step size is fixed at 17.5 uV; when it is less than −1.12 mV, the step size is fixed at −17.5 uV. Therefore, the maximum absolute step size is 17.5 uV. As used herein, "maximum step size" represents "maximum absolute step size". To show the importance of the effect that maximum absolute step size has on the presence of ringing artifacts in an output signal, two experiments were conducted. The results of the experiments are shown in FIGS. 10 and 11 and described herein.

Figure 10A:
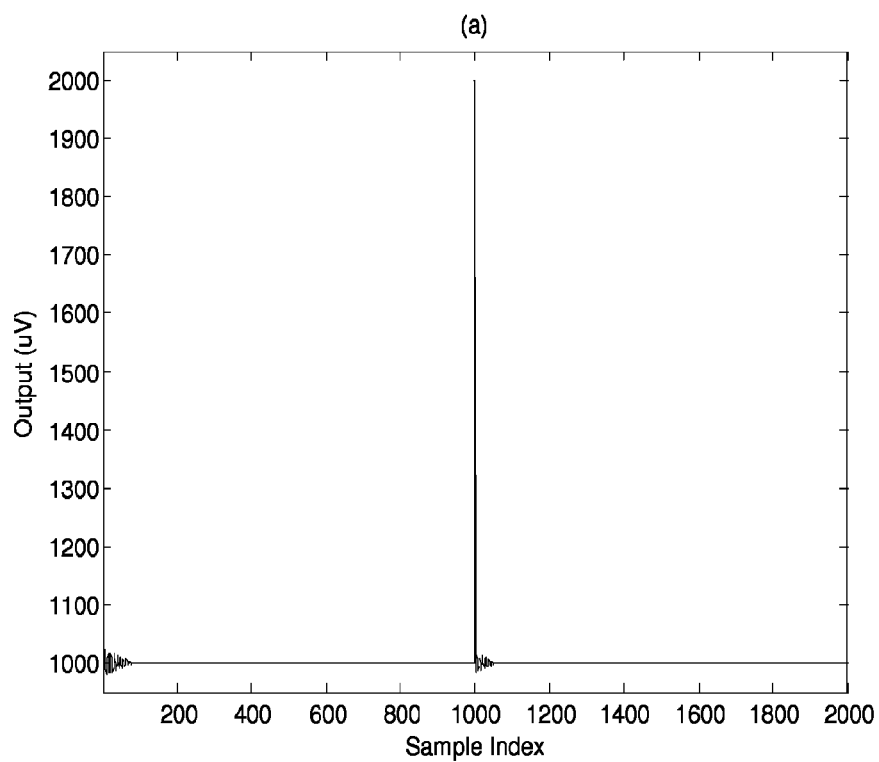
FIG. 10 is a graph showing the output of the notch filter having an upper bound value set at 17.5 uV when the input is a 1 mV DC signal with a 2 mV impulse at Sample 1000.
Figure 10B:
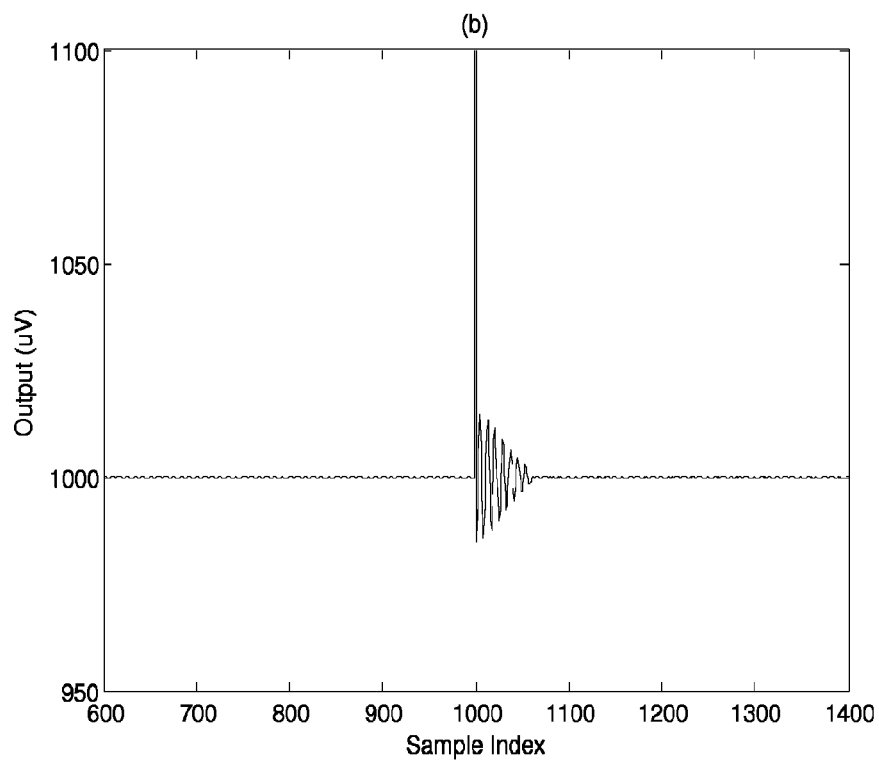
Figure 11A:
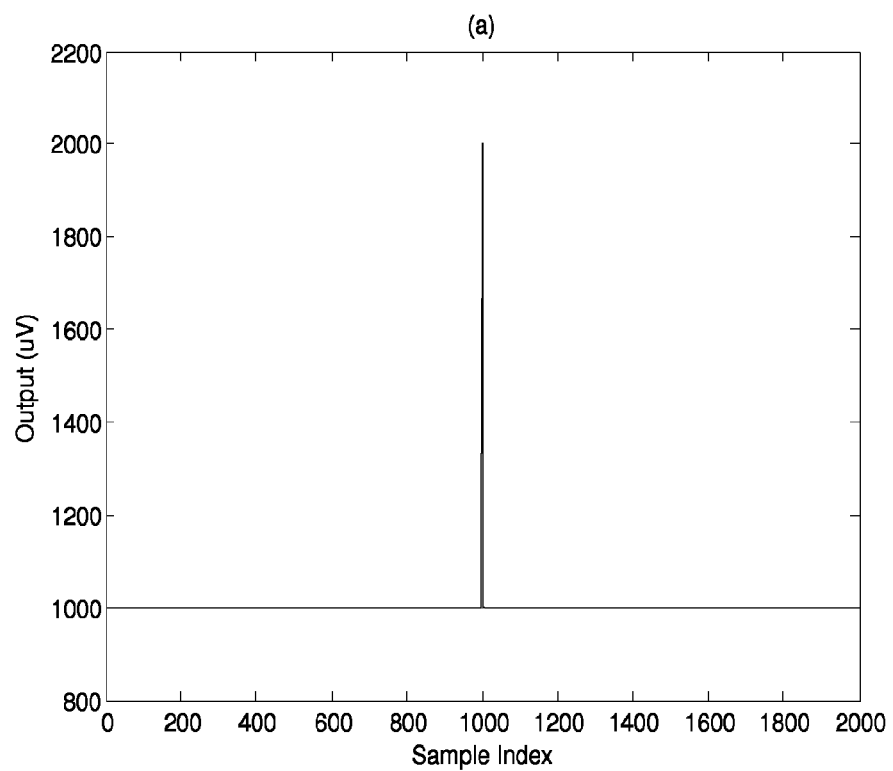
FIG. 11 is a graph showing the output of the notch filter having an upper bound value set at 1.75 uV when the input is a 1 mV DC signal with a 2 mV impulse at Sample 1000.
Figure 11B:
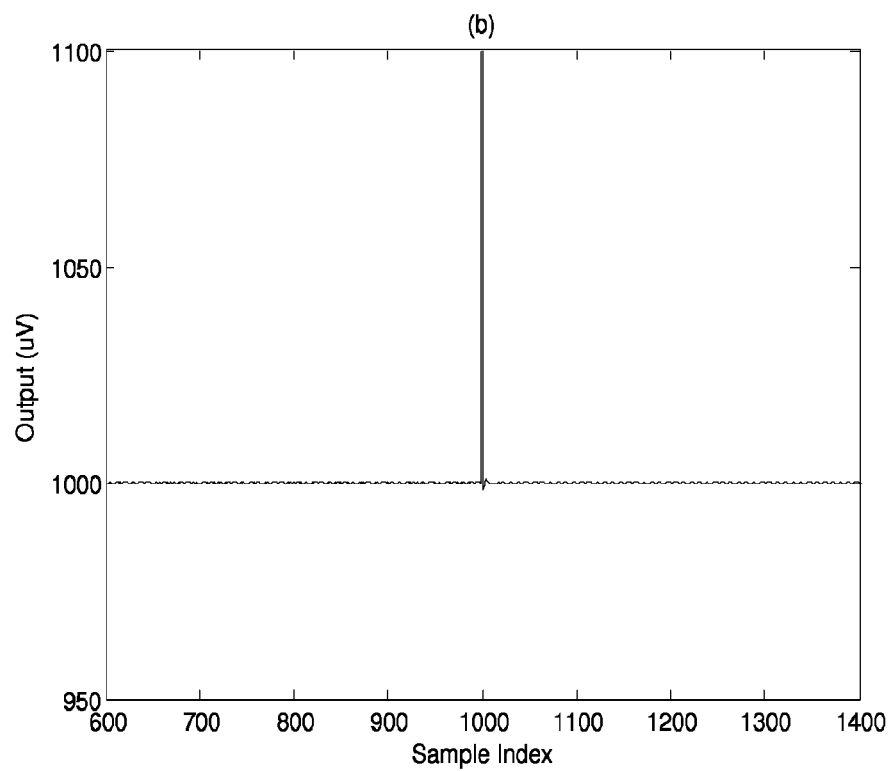

FIGS. 10A and 10B represent the results of a first experiment to investigate the impact of the maximum step size on the ringing problem. In both experiments, the input was a 1 mV DC signal with a 2 mV impulse at Sample 1000 and the notch frequency was set at 60 Hz. The sampling rate was 500 Hz. In the first experiment, the maximum step size was set to 17.5 uV and in the second experiment, the maximum step size was set to 1.75 uV.

FIG. 10A is a graphical overview of the results of the first experiment with FIG. 10B showing a more detailed view of the results at sample number 1000 when the 2 mV impulse was applied. A 2 mV impulse was used to simulate an input signal being sensed from a neonatal patient because the 2 mV impulse has aduration substantially the same as a duration of an neonatal QRS complex. At the time that the impulse was applied at sample 1000, there are perturbations in the output signal that represent the ringing artifact. The ringing artifact represents a period of perturbations in the output signal that last for a predetermined period of time (e.g. over a subsequent period of samples). The ringing artifact that results when the maximum step size is set to 17.5 uV is more clearly shown in FIG. 10B. Contrasting the results of the first experiment shown in FIGS. 10A and 10B with the results of the second experiment shown in FIGS. 11A and 11B where the maximum step size is set to 1.75 uV there is little to no ringing artifact when the step size is set at a value of 1.75 uV (e.g. below 10 uV). Thus, one can reasonably conclude that the step size being equal to 1.75 uV is preferable to the step size of 17.5 uV because the output signal produced using the lower step size value has significantly less ringing artifact associated therewith.

Figure 13:
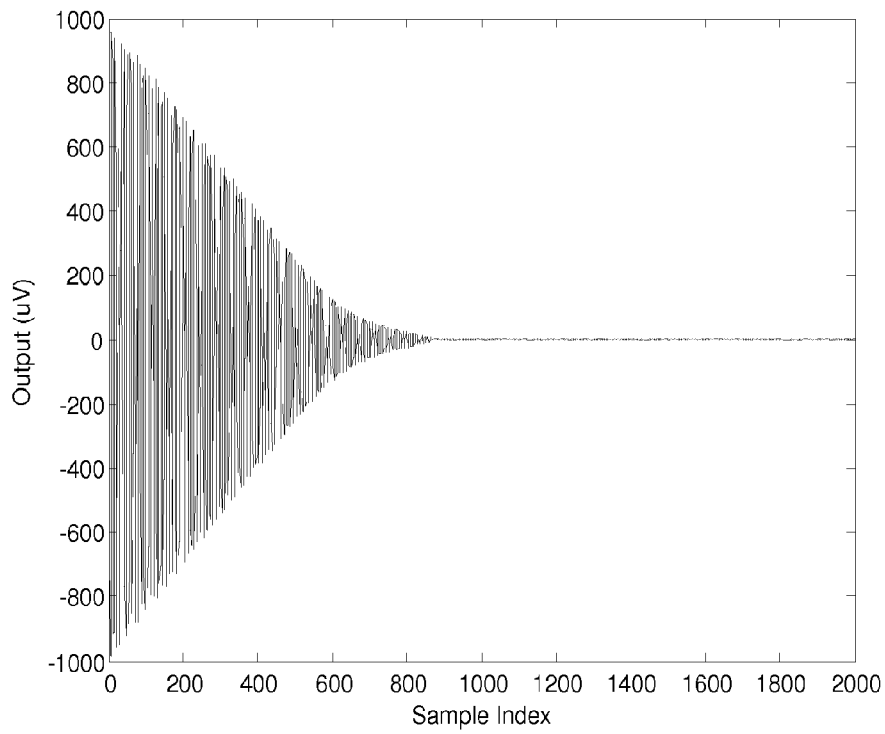
FIG. 13 is a graph showing the output of the notch filter when the input is a pure sinusoid signal.

However, since the main task of a notch filter is to remove sinusoid-like line interference, two additional experiments were conducted to investigate the impact of the maximum step size on the ability of the notch filter to effectively remove interference from an input signal. In both experiments, the input was a pure sinusoid with frequency at 60 Hz and amplitude at 1 mV and the notch frequency of the adaptive notch filter was set at 60 Hz while the sampling rate was set at 500 Hz. In a first experiment, the maximum step size for the notch filter was set equal to 17.5 uV and in a second experiment, the maximum step size for the notch filter was set equal to 1.75 uV. The results of the first experiment are shown in FIG. 12 and the results of the second experiment are shown in FIG. 13. As can be seen in FIGS. 12 and 13, the notch filter successfully removed the sinusoid interference. However, the filter with larger step size settles after 500 samples or 1 ms while the filter with smaller step size settles after 900 samples or 1.8 ms.

Therefore, it can be concluded from FIGS. 10-13, that the upper bound (maximum step size) determines the settling time and ringing effect on the output signal. Further, adaptive notch filters with larger upper bounds (greater maximum step sizes) take less time to settle, but may have severe ringing problems (see FIG. 10B). It is preferable that the filter settles quickly and has a minimal ringing artifact associated therewith which is a trade off that was considered when developing the adaptive notch filter that includes a maximum step size defined based on the type of patient (or input signal being filtered).

The adaptive notch filter according to invention principles which has a maximum step size (upper bound) defined based on the type of patient (or a characteristic of an input signal) advantageously employs the proper upper bound to generate an output signal that minimizes ringing artifacts but settles quickly. The ringing problem varies with QRS amplitude and duration. Higher amplitude and shorter duration results in more severe ringing. For example, a maximum R-wave amplitude for a QRS complex is substantially 5 mV and the shortest QRS duration ranges between substantially 15 ms to 20 ms. Thus, for the following discussion, an exemplary ECG waveform including a plurality of QRS complexes with amplitudes of 5 mV and each having a duration of 20 ms. Therefore, a bi-phasic triangle waveform with the above characteristics as shown in FIG. 14 advantageously illustrates the basis for choosing a particular maximum step value for a particular type of patient.

Figure 15:
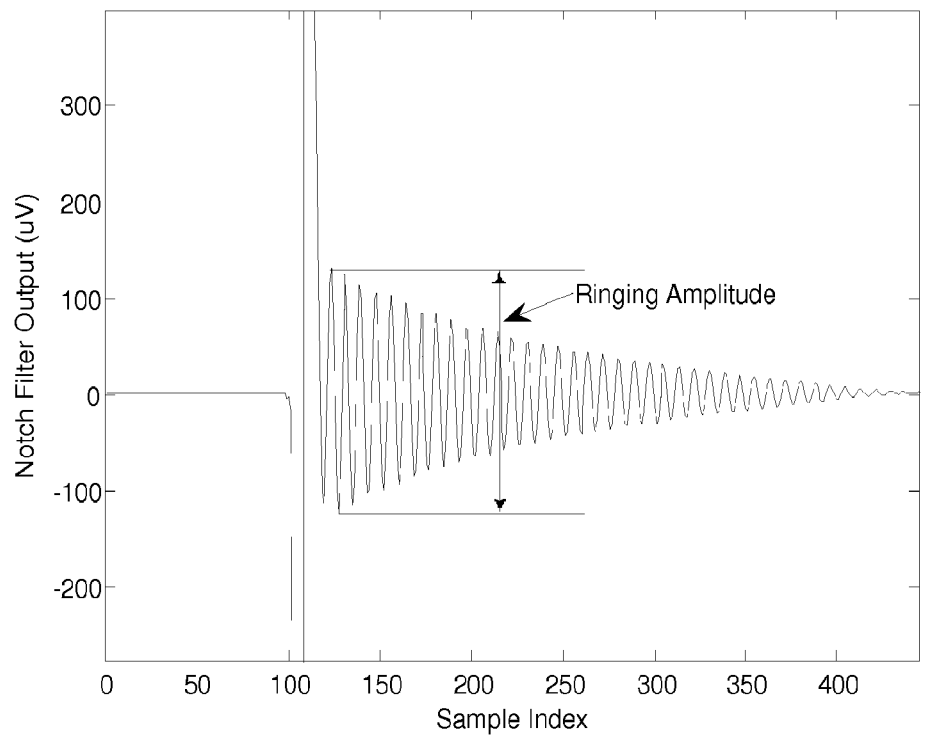
FIG. 15 is a graph defining the ringing amplitude.

An acceptable output signal filtered by the adaptive notch filter and used to generate ECG data has acceptable ringing amplitude of less than 10 uV. The acceptable ringing amplitude of less than 10 uV is due to the analog/digital resolution of the target system being 5 uV/bit and the presence of a filter with 6 dB attenuation in the ECG signal path. The ringing amplitude defined as the maximum peak-to-peak amplitude after the QRS complex. An example of ringing amplitude is shown in FIG. 15 wherein at sample 100 an impulse representative of a QRS complex was applied and the maximum peak-to-peak amplitude is shown.

Figure 14:
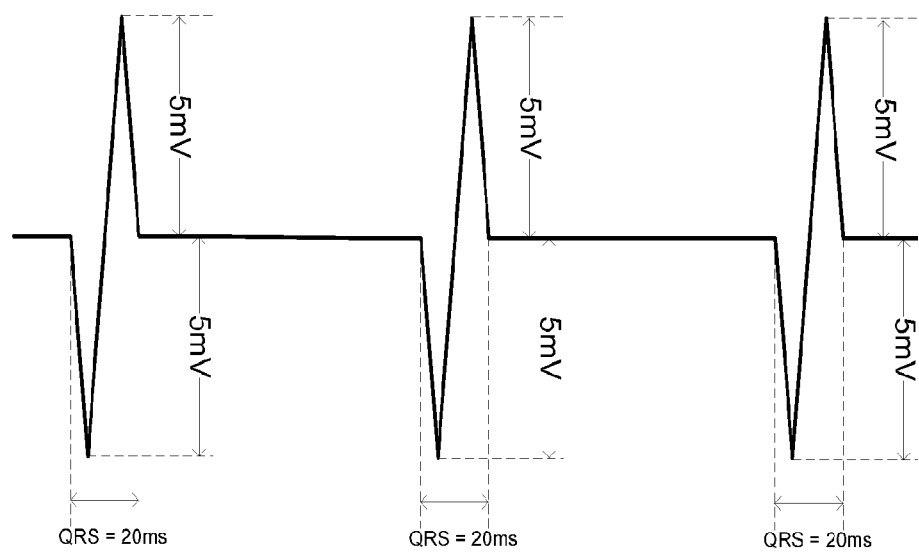
FIG. 14 is a simulated ECG used to determine the maximum step applied in the notch filter.

The exemplary ECG waveform shown in FIG. 14 was provided to a patient monitor. The heart rate was set to 60 bpm. A signal having 500 samples per second (sps) was extracted (including data for 30 seconds) from the patient monitor and used as the input to an offline notch filter to represent the effectiveness of minimizing ringing artifacts without negatively impacting the settling time of the signal. The extracted signal having 500 sps was applied at the input of the adaptive notch filter that implements an adaptive algorithm to estimate a level of interference in an input signal and remove the interference therefrom. A maximum step size implemented by the adaptive algorithm of the adaptive notch filter is selectively set by a user based on a type of patient and the characteristics of the QRS complex associated with patient of that type. The 500 sps signal collected from the patient monitor was fed into the notch filter and the ringing in the output was evaluated following the steps given below:

(1) Cut the output signal into 30 segments with 500 samples in each segment;

(2) Average all 30 segments to get the mean response; and (3) Manually find the maximum up-peak and minimum down-peak and calculate the peak-to-peak amplitude.

Thirteen different step size values that varied from 17.5 uV to 0.62 uV were tested. The step size settings and the corresponding ringing amplitude are presented in Table 2 and graphically represented in FIG. 16. Based on the data in Table 2 and shown in FIG. 16, in order to reduce the ringing amplitude below 10 uV, the maximum step size for a patient having a QRS complex with a high amplitude and short duration (e.g. a neonatal patient—as shown in the waveform in FIG. 14) is set less than 0.8 uV.

TABLE 2

Ringing amplitude versus maximum step size.

| Max step size Hex | Max step size (uV) | Ringing Amplitude (uV) |
|---|---|---|
| 0x70000 | 17.5000 | 254.4 |
| 0x60000 | 15.0000 | 230.2 |
| 0x50000 | 12.5000 | 199.4 |
| 0x40000 | 10.0000 | 163.9 |
| 0x30000 | 7.5000 | 125.4 |
| 0x20000 | 5.0000 | 83.8 |
| 0x10000 | 2.5000 | 39.0 |
| 0x9000 | 1.4063 | 19.7 |
| 0x8000 | 1.2500 | 17.2 |
| 0x7000 | 1.0938 | 14.8 |
| 0x6000 | 0.9375 | 12.5 |
| 0x5000 | 0.7813 | 10.2 |
| 0x4000 | 0.6250 | 8.4 |

The heart size of a neonate is usually very small resulting in the QRS-complex being narrow. Moreover, the tissue between the surface electrode connected to the patient and the heart of the neonatal patient is thin. Thus, the amplitude of the QRS-complex is usually high (e.g. up to 5 mV). Therefore, the QRS-complex is similar to an impulse and triggers the ringing artifact more easily. Adults and pediatrics usually have a longer QRS-complex, so even if the step size is large, the ringing artifact may not be triggered. To minimize the ringing artifact without negatively impacting the settling time of the signal for a neonatal patient, a maximum step size that is less than a maximum step size for a non-neonatal patient should be used. Therefore, the solution is to use small step size on neonates, and large step size on adults and pediatrics (e.g. non-neonatal patients).

Figure 16A:
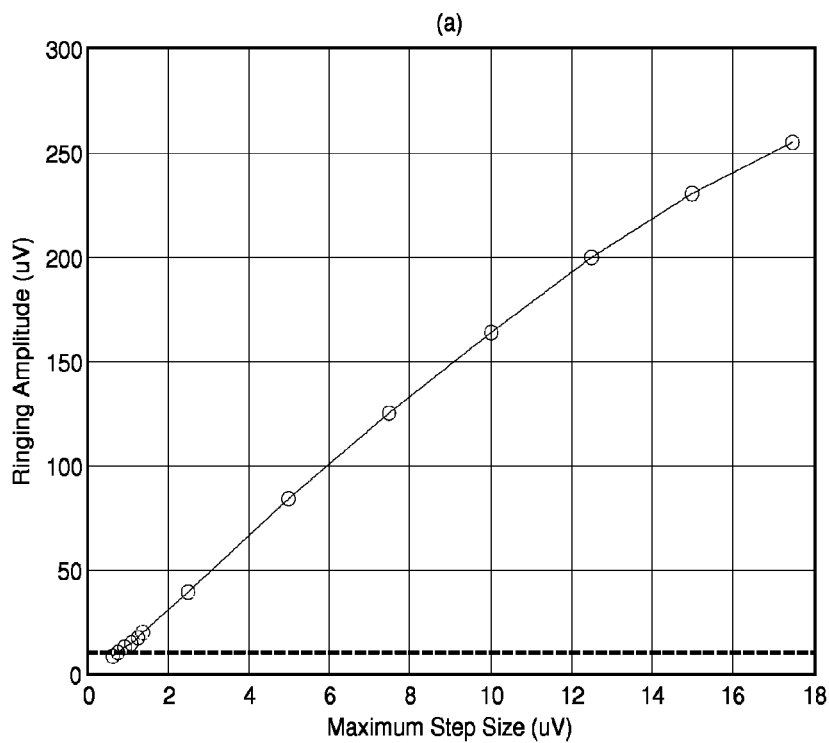
FIG. 16 is a graph showing the relationship between the ringing amplitude and maximum step size applied by the notch filter.
Figure 16B:
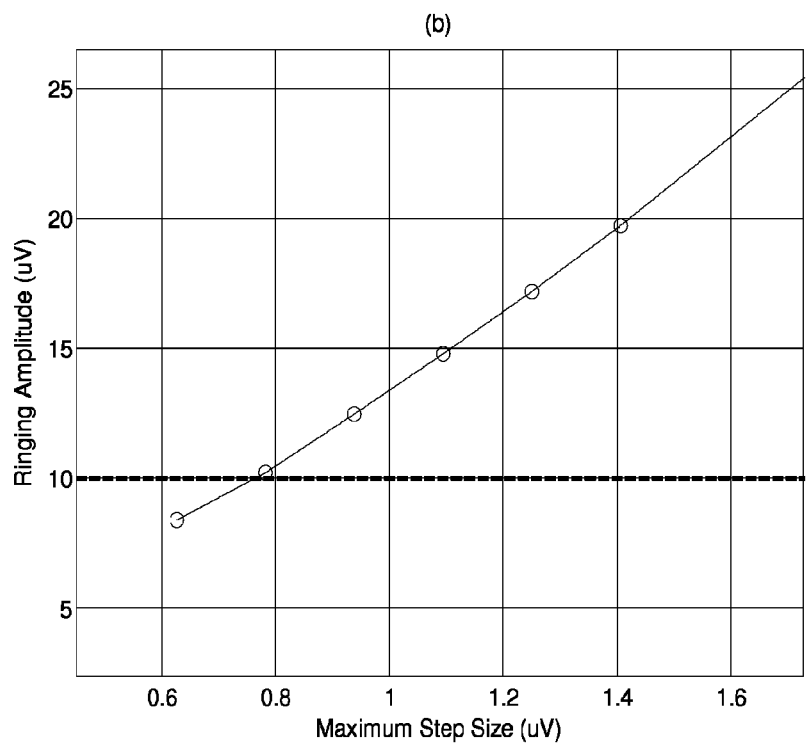

In view of the results shown in Table 2 and graphically represented in FIG. 16, the adaptive notch filter according to invention principles positioned within a patient monitoring device is selectively controlled to set a maximum step size for the filter based on the type of patient to which the monitor is connected. In a first mode of operation, the maximum step size of the adaptive notch filter is set based on the patient type being a neonatal patient. This results in a maximum step size in the first mode of operation being 0.78 uV. In a second mode of operation, the maximum step size of the adaptive notch filter is set based on the patient type being a non-neonatal patient. This results in a maximum step size in the second mode of operation being 17.5 uV. In one embodiment, the adaptive notch filter may include an initial setting wherein the patient type is pre-set as a non-neonatal patient and a default maximum step size setting be 17.5 uV.

While it is desirable to reduce the value for the maximum step size when the exemplary ECG waveform has a high amplitude and short duration, other factors need to be considered when determining a level for the maximum step size. These factors include
  (1) Settling time,
  (2) Recovery time,
  (3) Attenuation at notch frequency,
  (4) Response to distorted 60 Hz waveform, and
  (5) Response to real power line interference.

Because we are concerned with minimizing the ringing artifact in a neonatal ECG waveform, the patient monitor evaluates the above factors both "before" (17.5 uV) maximum step size was changed and "after" (0.78 uV) the maximum step size was changed.

The first factor considered is settling time. The settling time is the time required for the filter to reach the steady state response. FIG. 17A-17C shows the test results for the settling time. The results of this analysis were based on an input signal that was a pure sinusoid which was applied at Sample 500. The sinusoid signal had a frequency of 60 Hz and an amplitude of 1 mV. The sampling rate was 500 Hz. FIG. 17A represents the sinusoidal input signal. In FIG. 17B, the maximum step size is set equal to 17.5 uV and the settling time is substantially 1 second. When the maximum step size is reduced to 0.78 uV, the settling time is substantially 3 seconds.

The second factor considered is recovery time. Recovery time is important because, as the filter is an adaptive filter, the filter needs a predetermined period of time to "learn" when the signal is on and to "forget" when the signal is off. The time it takes for the filter to "forget" is the recovery time. FIGS. 18A-18C show the test results for the recovery time. FIG. 18A represents the sinusoidal input signal. In FIG. 18B, the maximum step size is set equal to 17.5 uV and the recovery time of substantially 1 second. When the maximum step size was reduced to 0.78 uV as shown in FIG. 18C, the recovery time is substantially 3 seconds. As can be seen the recovery time and settling time are highly correlated with one another.

A further factor considered is the ability to attenuate the input signal at the notch frequency. This is the most important measure of the notch filter. It describes how much interference can be removed from the interested signal. Since the adaptive notch filter has zeros right at the notch frequency, it has infinite attenuation at this frequency. Therefore, the residual should be the noise floor of the system. FIGS. 19A-19C show the test results for attenuation at the notch frequency. The input is a pure sinusoid with frequency at 60 Hz and amplitude at 1 mV. The sampling rate was 500 Hz. The outputs are the steady state responses of the filter. FIG. 19A represents a graph of the input signal described above. However, when looking to FIG. 19B which has a maximum step size set at 17.5 uV and FIG. 19C which has a maximum step size set at 0.78 uV, the 60 Hz input signal is attenuated to ±3.125 uV which is the noise floor of the filter. Thus, changing the maximum step size does not have impact on the attenuation of an interference signal.

A further factor to be considered is the effect that the maximum step size value may have when the input signal is distorted. A power line interference signal is close to a pure sinusoid with frequency at 60 Hz. However, the sinusoidal shape may be distorted due to various reasons. It may even be turned into a 60 Hz saw wave or square wave under certain circumstances. Therefore, it is important to characterize the response of the filter to square wave and saw wave when the maximum step size of the filter is set to 17.5 uV and 0.78 uV.

FIG. 20 shows the results when the input signal is a square wave. The input to the patient monitor was a symmetric biphasic square wave with frequency at 60 Hz and peak-to-peak amplitude at 10 mV. FIG. 20A indicates that the input to the notch filter is about 9.8 mV peak-to-peak. FIG. 20B indicates that the output signal corresponding to the 17.5 uV maximum step size is 2.1 mV peak-to-peak. In contrast, FIG. 20C indicates that the output signal corresponding to 0.78 uV step size is 3 mV peak-to-peak. The peak to peak amplitude associated with the maximum step size being 17.5 uV shows a slight performance improvement when attenuating a distorted square wave input signal.

FIG. 21 shows the results when the input signal is a saw wave. The input to the patient monitor was a rising saw wave with frequency at 60 Hz and peak-to-peak amplitude at 10 mV. FIG. 21A indicates that the input to the notch filter is about 7.3 mV peak-to-peak. FIG. 20B indicates that the output signal corresponding to the 17.5 uV maximum step size is 4.2 mV peak-to-peak. In contrast, FIG. 20C indicates that the output signal corresponding to 0.78 uV step size is 4.9 mV peak-to-peak. The peak to peak amplitude associated with the maximum step size being 17.5 uV shows a slight performance improvement when attenuating a distorted saw wave input signal.

While distortion response is important, a further measure of the effect of step size change on filter performance is associated with the response to real power line interference. A transformer was used to generate the real power line interference. The results are given in FIG. 22. It can be seen that the input to the notch filter is about 0.65 mV peak-to-peak shown in FIG. 22A. The output corresponding to the large step size is 0.39 mV peak-to-peak as shown in FIG. 22B and the output corresponding to the small step size is 0.42 mV peak-to-peak as shown in FIG. 22C. Similar to the responses to the distorted interference, FIG. 22 indicates that the larger step size provides slightly better attenuation to the real interference.

A summary of the outcomes of the factors considered and tested in FIGS. 17-22 is shown in Table 3. The reduction of the maximum step size solves the ringing problem with a minimal degradation to filter performance. This table may also serve as a reference for the notch filter performance difference between neonatal and non-neonatal (adults and pediatrics) patient.

TABLE 3

Performance comparison

| | Large max step size 17.5 uV (Adult, Pediatric) | Small max step size 0.78 uV (Neonatal) |
| --- | --- | --- |
| Ringing Amplitude | 254 uV | 10 uV |
| Settling time | 1 sec | 3 sec |
| Recovery time | 1 sec | 3 sec |
| 60 Hz Attenuation | Infinity (hit noise floor) | Infinity (hit noise floor) |
| Square wave attenuation | 13.4 dB | 10.3 dB |
| Saw wave attenuation | 4.8 dB | 3.5 dB |
| Transformer attenuation | 4.4 dB | 3.8 dB |

Figure 23A:
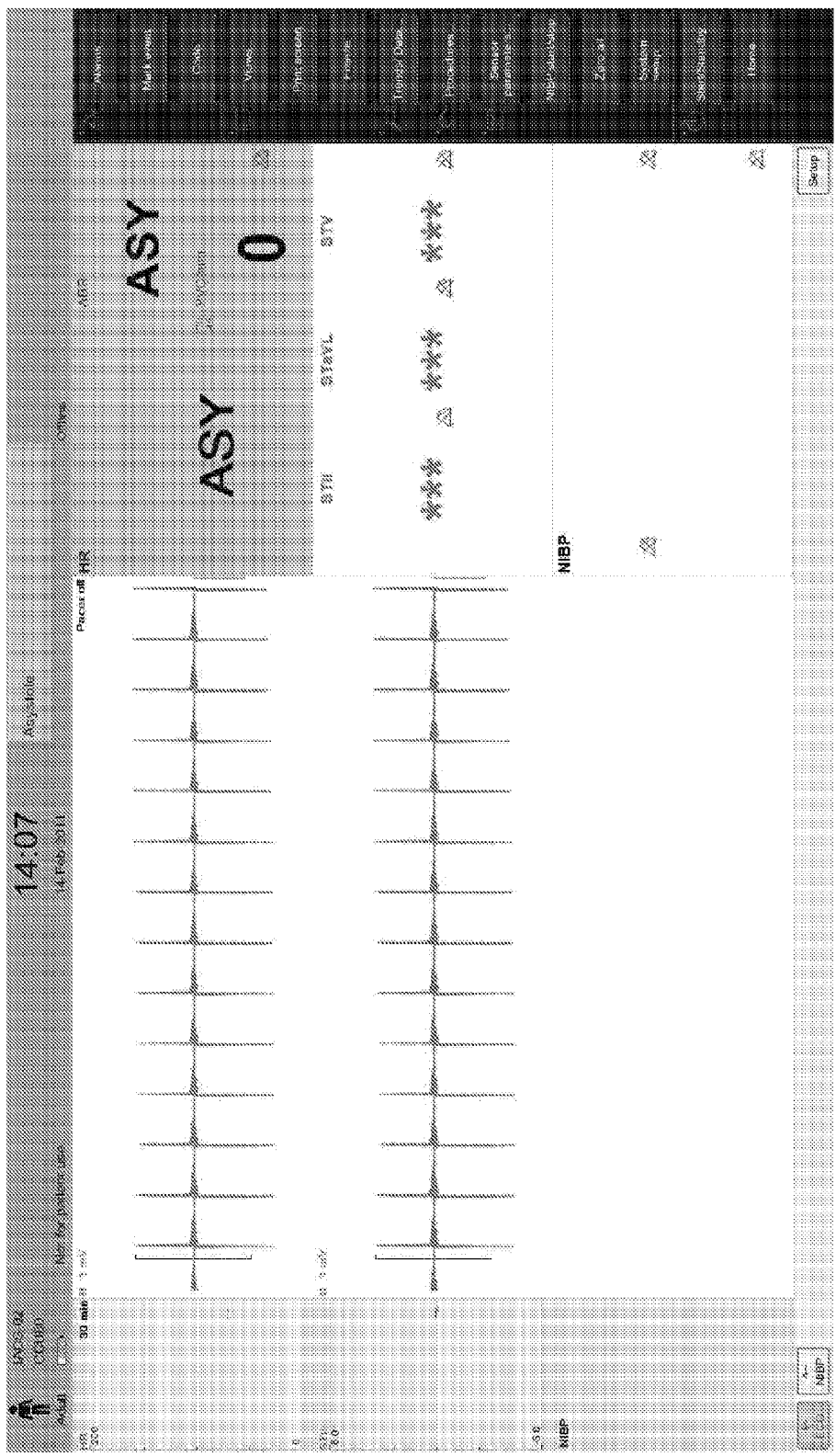
FIG. 23A shows ECG waveform displayed on the monitor for neonates after changing the maximum step size to 17.5 uV.
Figure 23B:
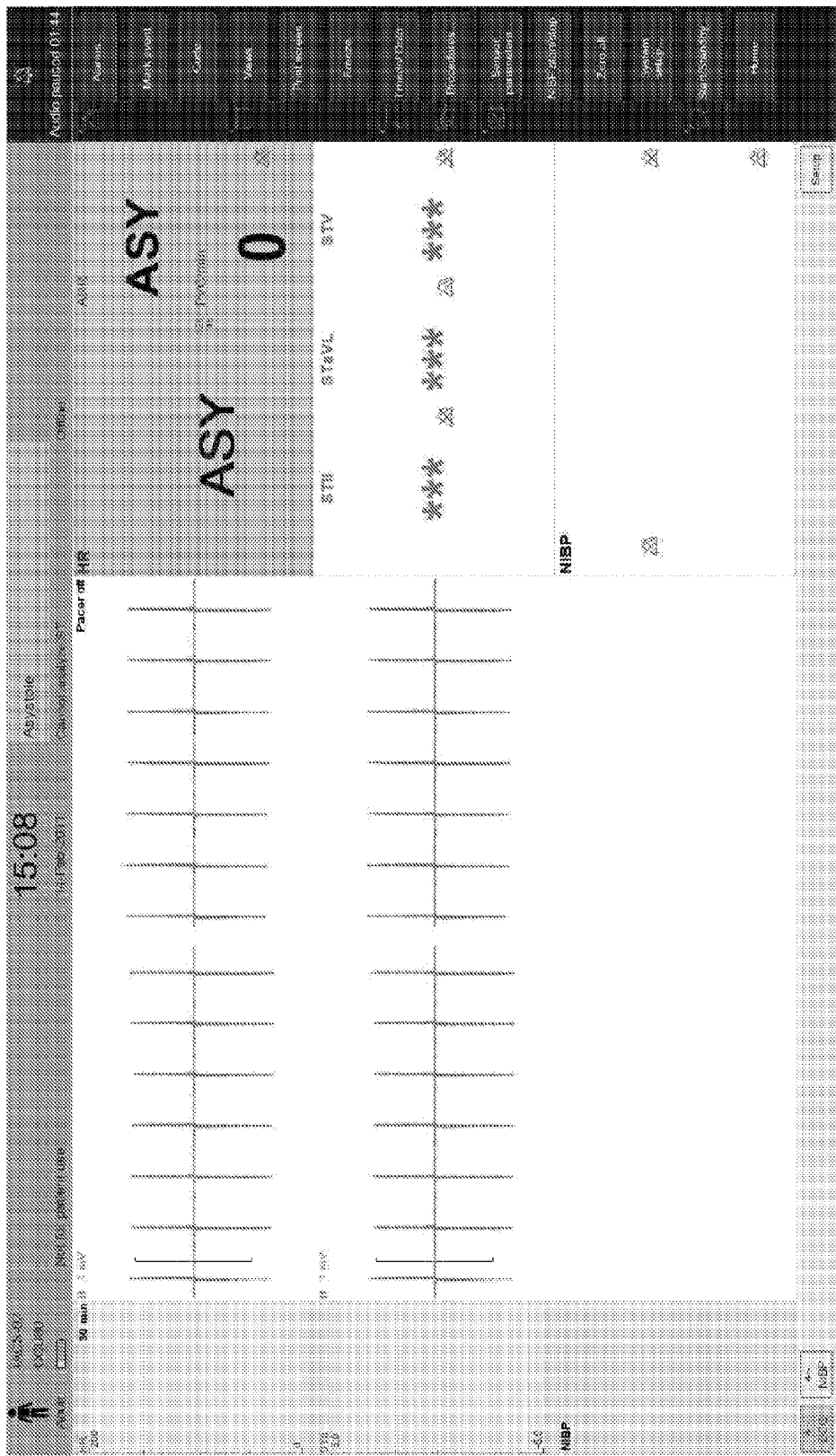
FIG. 23B shows ECG waveform displayed on the monitor for neonates after changing the maximum step size to 0.78 uV.

FIGS. 23A and 23B are exemplary screen shots from a patient monitoring device such as the one discussed above in FIGS. 2 and/or 4 showing an ECG waveform for a neonatal patient. In FIG. 23A, the maximum step size value for the adaptive notch filter is set at 17.5 uV and the resulting ECG waveform exhibits the ringing artifact. However, in FIG. 23B, the maximum step size value for the adaptive notch filter was reduce to 0.78 uV and there is no ringing artifact present in the resulting ECG waveform. Thus, by selectively controlling the filter parameter corresponding to the maximum step size, the adaptive notch filter advantageously minimizes the ringing artifact present in the ECG waveform derived from a neonatal patient without negatively impacting the settling time associated therewith.

Furthermore, as mentioned above, the ringing problem is related to short QRS duration and high R-wave amplitude which are characteristic of QRS complexes contained in neonatal ECG data. Thus, the filter parameter used by the adaptive notch filter is set to a different level as compared to non-neonatal patient. However, ECG data derived from non-neonatal patients may include QRS complexes that are similar to neonatal QRS complexes in that their durations may range substantially between 40~50 ms. In these instances, the ringing problem typically associated with neonatal may occur requiring a modification of the maximum step size being used by an adaptive filter when it is determined that a non-neonatal patient is exhibiting QRS complexes having a duration shorter than typical associated with non-neonatal patients.

Figure 24:
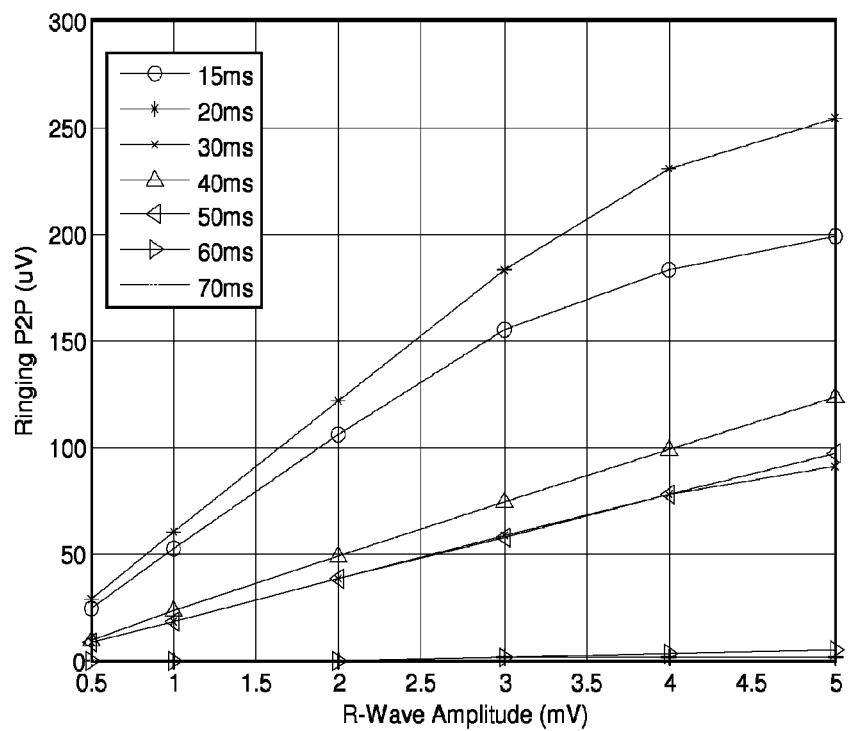
FIG. 24 is a graph showing the relationship between ringing and R-wave amplitude for given QRS durations.
Figure 25:
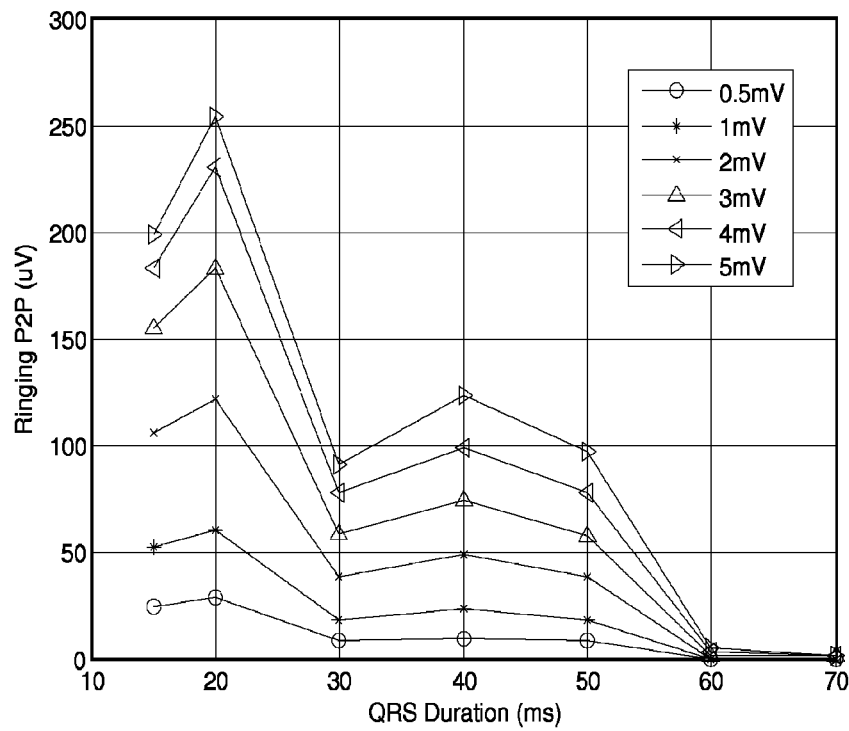
FIG. 25 is a graph showing the relationship between ringing and QRS duration for given R-wave amplitudes.

FIGS. 24 and 25 are graphical representations identifying under what condition the ringing artifact may appear using input signals having various QRS-durations and R-wave amplitudes. FIG. 24 shows the relationship between ringing artifact present on the target signal and R-wave amplitude for given QRS durations. Each curve shown in FIG. 24 corresponds to a fixed QRS duration. It can be seen in FIG. 24 that there is almost no ringing when the QRS duration is greater than 60 ms and there is unacceptable ringing when the QRS duration is 20 ms. However, it is important to note that the ringing artifact on target signals including QRS complexes having durations ranging between 40 ms and 50 ms is also significant.

FIG. 25 is a graph showing the relationship between ringing artifact present on the target signal and various QRS durations for given R-wave amplitudes. Each curve corresponds to a fixed R-wave amplitude. It can be seen in FIG. 25 that ringing artifact (as shown by the peak-to-peak amplitude) decreases when QRS duration increases despite the amplitude of the R-wave. The conclusion that can be drawn from the graphs in FIGS. 24 and 25 is that it is desirable to modify a filter parameter corresponding to the maximum step size for an adaptive notch filter when a duration value of QRS complexes for a respective patient is below a QRS duration value typically associated with a non-neonatal patient but above a QRS duration value typically associated with a neonatal patient. In one embodiment, when the configuration information identifies the patient as a non-neonatal patient and it is determined that the QRS complex duration value is less than the QRS complex duration value associated with a non-neonatal patient, the configuration processor (402 in FIG. 4) automatically controls the step processor (408 in FIG. 4) to modify the maximum step size value to be equal to a maximum step size value of a neonatal patient. This advantageously preserves any other monitoring settings contained in the configuration information and which are associated with a non-neonatal patient.

Table 4 shows the combination of QRS duration and R-wave amplitude that result in 10 uV ringing. For example, according to Table 4, if the QRS duration is 40 ms, the ringing will be noticeable (>10 uV) if the amplitude of the R-wave is above 0.52 mV.

TABLE 4

Duration and amplitude for 10 uV ringing

| QRS duration (ms) | R-wave amplitude corresponding to 10 uV ringing (mV) |
| --- | --- |
| 15 | 0.25 |
| 20 | 0.21 |
| 30 | 0.6 |
| 40 | 0.52 |
| 50 | 0.6 |
| 55 | 1.72 |
| 60 | >5 |
| 70 | >5 |

Thus, when the configuration processor is analyzing the characteristics of the patient parameter data, the values in Table 4 may be used to determine whether or not the analyzed characteristic of the patient parameter will produce an unacceptable level of ringing in the target signal. This advantageously enables the configuration processor to control the step processor to automatically and in real-time, modify the step size value for the adaptive notch filter.

The apparatus discussed above with respect to FIGS. 2-25 advantageously provide a patient monitoring device that includes an adaptive notch filter having a filter parameter, the value of which, is selectively controlled based on the type of input signal to be filtered as well as an amount of ringing artifact present on a target signal output by the adaptive notch filter and used to determine at least one patient parameter. By minimizing the ringing artifact on the target signal, one improves the ability to determine and monitor at least one patient parameter. The apparatus further advantageously provides a feedback control of the adaptive notch filter by analyzing characteristics of the determined patient parameters to see if the characteristics present match characteristics known to be associated with a selected type of input signal. Based on the outcome of the analysis, the filter parameter associated with the type of input signal that is being used by the adaptive notch filter may be automatically modified to ensure that the target signal will maintain the ringing artifact below the threshold level. This automatic and real time modification of the filter parameter further advantageously maintains any other monitor settings that were selected and which are associated with the selected signal type.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

We claim:
1. A patient monitoring device that determines and monitors at least one patient parameter comprising:
   a configuration processor that generates configuration information in response to a first input signal identifying a type of patient connected to the patient monitoring device;
   an adaptive notch filter that receives a sensed physiological input signal, the sensed physiological input signal including a signal of interest and an interference signal in a predetermined frequency range, and the adaptive notch filter automatically estimates the interference signal within the sensed physiological input signal and removes the estimated interference signal from the sensed physiological input signal to generate a target signal; and
   a step processor electrically coupled between the configuration processor and the adaptive notch filter that sets a value of a filter parameter based on the type of patient using the configuration information, wherein the adaptive notch filter uses the filter parameter associated with the type of patient to estimate the interference signal within the sensed physiological input signal and reduce a ringing artifact on the target signal below a threshold level upon removal of the interference signal from the sensed physiological input signal, and wherein the step processor sets the value of the filter parameter equal to a first value when the configuration information indicates that the sensed physiological input signal is acquired from a patient of a first type and sets the value of the filter parameter equal to a second value greater than the first value when the configuration information indicates that the sensed physiological input signal is acquired from a patient of a second type.

2. The apparatus as recited in claim 1, wherein
the filter parameter is an maximum absolute step size value that is set with respect to the configuration information associated with the type of patient.

3. The apparatus as recited in claim 1, wherein
the filter parameter represents a step size associated with the type of patient.

4. The apparatus as recited in claim 1, wherein
the configuration information representing the type of patient is indicative of one of a neonatal patient or a non-neonatal patient.

5. The apparatus as recited in claim 1, wherein
the step processor sets the filter parameter at a value that reduces the ringing artifact of the target signal below 10 microvolts.

6. The apparatus as recited in claim 1, further comprising
a parameter processor, electrically coupled to an output of the adaptive notch filter, receives the target signal and selectively determines data representing the at least one patient parameter from the target signal; and
the configuration processor determines if a characteristic of the at least one patient parameter is within a threshold range and, in response to a determination the characteristic is outside the threshold range, automatically controls the step processor to modify the filter parameter value from a current filter parameter value associated with the type of patient indicated by the first input signal to a second different filter parameter associated with a different type of patient.

7. The apparatus of claim 1, further comprising
a user interface, electrically coupled to the configuration processor, that enables a user to provide the first input signal representing the type of patient for use in generating the configuration information.

8. The method as recited in claim 1, wherein the activity of setting the filter parameter further comprises
setting a step size value associated with a particular type of patient.

9. The apparatus as recited in claim 6, wherein
the step processor automatically modifies the filter parameter value to be set at a value that maintains the ringing artifact on the target signal below the threshold level.

10. The apparatus of claim 6, wherein
the at least one patient parameter is ECG data including a plurality of QRS complexes and the characteristic of the at least one patient parameter is a duration of respective QRS complexes.

11. The apparatus of claim 10, wherein
the configuration processor compares a duration value of at least one QRS complex to an upper threshold value and a lower threshold value to determine if the QRS complex duration is within a predetermined range of QRS complex durations associated with the sensed physiological input signal from the type of patient indicated by the first input signal.

12. The apparatus of claim 11, wherein
the step processor, in response to a determination, that the QRS complex duration is outside the predetermined range, automatically modifies the filter parameter value to maintain a ringing artifact on the target signal below the threshold level.

13. A method of removing an interference signal from an input signal in a patient monitoring device that determines and monitors at least one patient parameter, the method comprises the activities of:

generating, by a configuration processor, configuration information in response to a first input signal identifying a type of patient connected to the patient monitoring device;

setting, by a step processor coupled to the configuration processor, a value of a filter parameter based on the type of patient using the configuration information by:

setting the value of the filter parameter equal to a first value when the configuration information indicates that a sensed physiological input signal is acquired from a patient of a first type and setting the value of the filter parameter equal to a second value greater than the first value when the configuration information indicates that the sensed physiological input signal is acquired from a patient of a second type;

receiving the sensed physiological input signal at an adaptive notch filter coupled to the step processor, the sensed physiological input signal including a signal of interest and an interference signal in a predetermined frequency range;

using, by the adaptive notch filter, the filter parameter associated with the type of patient to automatically estimate the interference signal within the sensed physiological input signal and reduce a ringing artifact on the target signal below a threshold level upon removal of the interference signal from the sensed physiological input signal.

14. The method as recited in claim 13, wherein the activity of setting the filter parameter value further comprises setting an maximum absolute step size value for the adaptive notch filter with respect to the configuration information.

15. The method as recited in claim 13, wherein the activity setting the filter parameter using the configuration information representing the type of patient includes one of setting a first value that indicates a neonatal patient and setting the filter parameter to a second value that indicates a non-neonatal patient.

16. The method as recited in claim 13, wherein the activity of setting further comprises setting the filter parameter representing the step size at a value able to reduce the ringing artifact of the target signal below 10 microvolts.

17. The method as recited in claim 13, further comprising the activities of receiving the target signal by a parameter processor that is electrically coupled to an output of the adaptive notch filter;

selectively determining data representing the at least one patient parameter from the target signal;

determining, by the configuration processor, if a characteristic of the at least one patient parameter is within a threshold range; and automatically controlling the step processor to modify the filter parameter value from a current filter parameter value associated with the type of patient indicated by the first input signal to a second different filter parameter associated with a different type of patient in response to a determination the characteristic is outside the threshold range.

18. The method of claim 13, further comprising the activity of inputting information identifying the type of patient to provide the first input signal at a user interface electrically coupled to the configuration processor; and using the information to generate the configuration information.

19. The method as recited in claim 17, wherein activity of automatically modifying the filter parameter value includes setting the filter parameter value to be set at a value that maintains the ringing artifact on the target signal below the threshold level.

20. The method of claim 17, wherein the at least one patient parameter is ECG data including a plurality of QRS complexes and the characteristic of the at least one patient parameter is a duration of respective QRS complexes.

21. The method of claim 20, further comprising the activity of comparing, by the configuration processor, a duration value of at least one QRS complex to an upper threshold value and a lower threshold value to determine if the QRS complex duration is within a predetermined range of QRS complex durations associated with the sensed physiological input signal from the type of patient indicated by the first input signal.

22. The method of claim 21, further comprising the activity of automatically modifying the filter parameter by the step processor, in response to a determination that the QRS complex duration is outside the predetermined range to maintain a ringing artifact on the target signal below the threshold level.

23. An apparatus for removing an interference signal from an input signal in a patient monitoring device that determines and monitors at least one patient parameter, the apparatus comprising:

means for generating configuration information in response to a first input signal identifying a type of patient connected to the patient monitoring device as being either neonatal or non-neonatal;

means for setting a value of a filter parameter based on the type of patient using the configuration information by:

setting the value of the filter parameter equal to a first value when the configuration information indicates that a sensed physiological input signal is acquired from a patient of a first type and setting the value of the filter parameter equal to a second value greater than the first value when the configuration information indicates that the sensed physiological input signal is acquired from a patient of a second type;

means for receiving the sensed physiological input signal at an adaptive notch filter, the sensed physiological input signal including a signal of interest and an interference signal in a predetermined frequency range;

means for using, by the adaptive notch filter, the filter parameter associated with the type of patient to automatically estimate the interference signal within the sensed physiological input signal and reduce a ringing artifact on the target signal below a threshold level upon removal of the interference signal from the sensed physiological input signal.

24. A patient monitoring device that determines and monitors at least one patient parameter comprising:

a configuration processor that generates configuration information in response to a first input signal identifying a type of a patient connected to the patient monitoring device as being either neonatal or non-neonatal;

an adaptive notch filter that receives a sensed physiological input signal, the sensed physiological input signal including a signal of interest and an interference signal in a predetermined frequency range, and the adaptive notch filter automatically estimates the interference signal within the sensed physiological input signal and removes the estimated interference signal from the sensed physiological input signal to generate a target signal; and a step processor electrically coupled between the configuration processor and the adaptive notch filter that sets a value of a filter parameter based on the type of patient using the configuration information, wherein the adaptive notch filter uses the filter parameter associated with the type of patient to estimate the interference signal within the sensed physiological input signal and reduce a ringing artifact on the target signal below a threshold level upon removal of the interference signal from the sensed physiological input signal, and wherein the step processor sets the value of the filter parameter equal to a first value when the configuration information indicates that the sensed physiological input signal is acquired from a patient of a first type and sets the value of the filter parameter equal to a second value greater than the first value when the configuration information indicates that the sensed physiological input signal is acquired from a patient of a second type.

25. A patient monitoring device that determines and monitors at least one patient parameter comprising:

a configuration processor that generates configuration information in response to a first input signal identifying a type of patient connected to the patient monitoring device;

an adaptive notch filter that receives a sensed physiological input signal, the sensed physiological input signal including a signal of interest and an interference signal in a predetermined frequency range and removes the interference signal from the sensed physiological input signal to generate a target signal; and a step processor electrically coupled between the configuration processor and the adaptive notch filter that sets a value of a filter parameter based on the type of patient using the configuration information, wherein the adaptive notch filter uses the filter parameter associated with the type of patient to remove the interference signal within the sensed physiological input signal and reduce a ringing artifact on the target signal below a threshold level upon removal of the interference signal from the sensed physiological input signal, and wherein the step processor sets the value of the filter parameter equal to a first value when the configuration information indicates that the sensed physiological input signal is acquired from a patient of a first type and sets the value of the filter parameter equal to a second value greater than the first value when the configuration information indicates that the sensed physiological input signal is acquired from a patient of a second type.

* * * * *